(12) United States Patent
Minatelli et al.

(10) Patent No.: US 9,610,313 B2
(45) Date of Patent: Apr. 4, 2017

(54) EYE HEALTH COMPOSITION AND METHOD USING PLANT DERIVED SEED EXTRACT RICH IN ESSENTIAL FATTY ACIDS DERIVED FROM PERILLA SEED AND CAROTENOIDS

(71) Applicant: U.S. NUTRACEUTICALS, LLC, Eustis, FL (US)

(72) Inventors: John A. Minatelli, Mount Dora, FL (US); W. Stephen Hill, Ocala, FL (US); Rudi E. Moerck, Sanford, FL (US); Uy Nguyen, Eustis, FL (US)

(73) Assignee: U.S. NUTRACEUTICALS, Eustis, FL (US)

( * ) Notice: Subject to any disclaimer, the term of this patent is extended or adjusted under 35 U.S.C. 154(b) by 390 days.

(21) Appl. No.: 14/275,968

(22) Filed: May 13, 2014

(65) Prior Publication Data
US 2014/0248369 A1    Sep. 4, 2014

Related U.S. Application Data

(63) Continuation-in-part of application No. 13/231,131, filed on Sep. 13, 2011, now Pat. No. 8,784,904, which is a continuation-in-part of application No. 12/419,321, filed on Apr. 7, 2009, now Pat. No. 8,586,104.

(60) Provisional application No. 61/043,773, filed on Apr. 10, 2008.

(51) Int. Cl.
| | |
|---|---|
| *A61K 36/535* | (2006.01) |
| *A61K 36/185* | (2006.01) |
| *A61K 31/122* | (2006.01) |
| *A61K 36/05* | (2006.01) |
| *A61K 35/612* | (2015.01) |
| *A61K 36/02* | (2006.01) |
| *A23D 9/00* | (2006.01) |
| *A61K 36/537* | (2006.01) |
| *C11B 1/06* | (2006.01) |
| *C11B 1/10* | (2006.01) |
| *C11B 3/00* | (2006.01) |
| *A61K 31/07* | (2006.01) |
| *A61K 31/201* | (2006.01) |
| *A23L 33/105* | (2016.01) |
| *A23L 33/115* | (2016.01) |

(52) U.S. Cl.
CPC .............. *A61K 36/535* (2013.01); *A23D 9/00* (2013.01); *A23L 33/105* (2016.08); *A23L 33/115* (2016.08); *A61K 31/07* (2013.01); *A61K 31/122* (2013.01); *A61K 31/201* (2013.01); *A61K 35/612* (2013.01); *A61K 36/02* (2013.01); *A61K 36/05* (2013.01); *A61K 36/537* (2013.01); *C11B 1/06* (2013.01); *C11B 1/10* (2013.01); *C11B 1/104* (2013.01); *C11B 3/001* (2013.01); *A61K 2236/15* (2013.01); *A61K 2236/37* (2013.01)

(58) Field of Classification Search
None
See application file for complete search history.

(56) References Cited

U.S. PATENT DOCUMENTS

| | | | |
|---|---|---|---|
| 5,332,803 A | 7/1994 | Miyazaki et al. | |
| 5,527,533 A | 6/1996 | Tso et al. | |
| 5,533,527 A | 7/1996 | Terman | |
| 5,585,400 A | 12/1996 | Cook et al. | |
| 6,123,965 A | 9/2000 | Jacob et al. | |
| 6,552,081 B1 | 4/2003 | Freedman et al. | |
| 6,827,965 B1 | 12/2004 | Fitzpatrick | |
| 7,959,950 B2 | 6/2011 | Evans et al. | |
| 8,030,037 B2 | 10/2011 | Thomas et al. | |
| 8,084,071 B2 | 12/2011 | Miyake et al. | |
| 8,586,104 B2 | 11/2013 | Minatelli et al. | |
| 8,652,544 B2 | 2/2014 | Minatelli et al. | |
| 8,784,904 B2 * | 7/2014 | Minatelli | A23L 33/105 424/725 |
| 9,114,142 B2 * | 8/2015 | Minatelli | A23L 33/105 |
| 9,138,452 B2 * | 9/2015 | Minatelli | A23L 33/105 |
| 9,511,106 B2 * | 12/2016 | Minatelli | A23L 33/105 |
| 2002/0155182 A1 | 10/2002 | Belna | |
| 2002/0168431 A1 | 11/2002 | Belna | |
| 2003/0175403 A1 | 9/2003 | Gurin | |
| 2004/0137132 A1 | 7/2004 | Nunez et al. | |
| 2004/0185129 A1 | 9/2004 | Vuksan | |
| 2005/0260145 A1 | 11/2005 | Leigh et al. | |
| 2006/0127505 A1 | 6/2006 | Haines et al. | |
| 2006/0147564 A1 | 7/2006 | Kim | |
| 2007/0185340 A1 | 8/2007 | Van Toor et al. | |
| 2007/0266774 A1 | 11/2007 | Gibson et al. | |
| 2008/0095881 A1 | 4/2008 | Ber | |
| 2008/0305096 A1 | 12/2008 | Verdegem et al. | |
| 2008/0305190 A1 | 12/2008 | Vuksan | |
| 2009/0048339 A1 | 2/2009 | Kanwar et al. | |
| 2009/0181114 A1 | 7/2009 | Minatelli et al. | |
| 2009/0181127 A1 | 7/2009 | Minatelli et al. | |
| 2009/0258081 A1 | 10/2009 | Minatelli et al. | |
| 2010/0144878 A1 | 6/2010 | Popp | |
| 2010/0216885 A1 | 8/2010 | Kabaradjian | |
| 2010/0260893 A1 | 10/2010 | Kabaradjian | |
| 2010/0303999 A1 | 12/2010 | Chungu et al. | |
| 2012/0027787 A1 | 2/2012 | Minatelli et al. | |

FOREIGN PATENT DOCUMENTS

| | | |
|---|---|---|
| CN | 1369290 | 9/2002 |
| CN | 1583009 | 2/2005 |

(Continued)

OTHER PUBLICATIONS

Database WPI, Week 200676, Thomson Scientific, Apr. 2006, 1 pg.

(Continued)

*Primary Examiner* — Chris R Tate
*Assistant Examiner* — Randall Winston
(74) *Attorney, Agent, or Firm* — Allen, Dyer, Doppelt, Milbrath & Gilchrist, P.A.

(57) ABSTRACT

A dietary supplement composition is formulated in a therapeutically effective amount to treat the eye of an individual. The composition includes a *perilla* seed oil extract, astaxanthin, and at least one carotenoid selected from the group consisting of lutein, trans-zeaxanthin and meso-zeaxanthin.

9 Claims, 2 Drawing Sheets

(56) References Cited

FOREIGN PATENT DOCUMENTS

| CN | 1912081 | 2/2007 |
|---|---|---|
| DE | 10008948 | 8/2001 |
| EP | 0941672 | 9/1999 |
| JP | 6310816 | 8/1988 |
| JP | 401056793 | 3/1989 |
| WO | 99/62356 | 9/1999 |
| WO | 02/072119 | 9/2002 |
| WO | 2004/022725 | 3/2004 |
| WO | 2006040596 | 4/2006 |
| WO | 2009126798 | 10/2009 |

OTHER PUBLICATIONS

Database WPI, Week 200712, Thomson Scientific, Sep. 2006, pp. 1-2.
Database GNPD, Mintel, "Slimming Tea", Apr. 2013, pp. 1-4.
Database GNPD, Mintel, "Yonsei Milk: Omega-3 Perilla Soy Milk", May 2012, pp. 1-4.
"Valensa Launches Broad New Portfolio of Perilla-based Formulations", Press Release, Mar. 2013, pp. 1-4.
Kim et al., "Supercritical carbon dioxide extraction of perilla seed oil" Korean Society of Food Science and Technology, vol. 5, No. 4, 1996, pp. 300-304.
Cho et al., "Effects of defatted safflower and perilla seed powders on lipid metabolism in ovariectomized female rats fed high cholesterol diets", Journal of the Korean Society of Food Science and Nutrition, vol. 30, No. 1, Feb. 2001, pp. 1-2.
"Perilla oil, a source of heart-healthy alpha-linolenic acid", Life Extension Magazine, Apr. 2004, pp. 1-4.
Asif, "Health effects of omega-3,6,9 fatty acids: perilla frutescens is a good example of plant oils", Oriental Pharmacy and Experimental Medicine, vol. 11, No. 1, Mar. 2011, pp. 1-9.
Asif et al., "Nutritional and functional characterisations of perilla frutescens seed oil and evaluation of its effect on gastrointestinal motility", Malaysian Journal of Pharmaceutical Sciences, 2010, pp. 1-12.
2001-280848, DW, Apr. 3, 2001.
Shin et al., "Lipid Composition of Perilla Seed," Journal of the American Oil Chemists, vol. 71, No. 6, Jan. 1994, pp. 619-622.
Asif, Health Effects of Omega-3, 6, 9 Fatty Acids: Perilla Frutescens is a Good Example of Plant Oils,: Oriental Pharmacy & Experimental Medicine, vol. 11, No. 1, Mar. 2011, pp. 51-59.
Przybylski, "Flax Oil and High Linelenic Oils," Bailey's Industrial Oil and Fat Products, Jan. 2005, pp. 281-301.
Life Extension Magazine, "Perilla Oil a Source of Heart-Healthy Alpha-Linolenic Acid," Jan. 2004, pp. 1-4.
Database GNPD, "Entrox Dietary Supplement," Aug. 2001, p. 1.
Asif, "Nutritional and Functional Characterisation of Perilla Frutescens Seed Oil and Evaluation of its Effect on Gastrointestinal Motility." Malaysian Journal of Pharmaceutical Sciences, Jan. 2010, pp. 1-12.
"Valensa Introduces Tresalbio™ Salvia Hispanica Seed CO2 Extract," Oct. 9, 2006, Retrieved from the Internet: http://www.usnutra.com/resources/news/Seed-CO2.php, 2 pages.
Coates et al., "Commercial Production of Chia in Northwestern Argentina," Journal of the American Oil Chemists' Society, vol. 75, No. 10, 1998, pp. 1417-1420.
"Valensa Launches O2B™ Peroxidation Blocker Technology at Vitafoods 2006," Jun. 8, 2006, Retrieved from the Internet: http://www.usnutra.com/resources/news/Technology-Vitafoods.php, 1 page.
Surette et al., "Inhibition of Leukotriene Synthesis, Pharmacokinetics, and Tolerability of a Novel Dietary Fatty Acid Formulation in Healthy Adult Subjects," Clinical Therapeutics, vol. 25, No. 3, Mar. 2003, pp. 948-971.
Reverchon et al., "Supercritical Fluid Extraction and Fractionation of Natural Matter," Journal of Supercritical Fluids, vol. 38, No. 2, Sep. 1, 2006, pp. 146-166.
Illes et al., "Extraction of Hiprose Fruit by Supercritical CO2 and Propane," Journal of Supercritical Fluids, vol. 10, No. 3, Aug. 1, 1997, pp. 209-218.
Catchpole et al., "Extraction of Seed Oils Using Supercritical CO2 and Subcritical Propane," Proceedings of the 2nd International Meeting on High Pressure, 2001, pp. 1-13.
Taga et al., "Chia Seeds as a Source of Natural Lipid Antioxidants," Journal of the American Oil Chemists' Society, 1984 Department of Foods and Nutrition, Purdue University, West Lafayette, Indiana, vol. 61, No. 5, May 1984, pp. 928-931.
List et al., "Oxidative Stability of Seed Oils Extracted with Supercritical Carbon Dioxide," Journal of the American Oil Chemists' Society, vol. 66, No. 1, Jan. 1, 1989, pp. 98-101.
Gomez et al., "Recovery of Grape Seed Oil by Liquid and Supercritical Carbon Dioxide Extraction: A Comparison with Conventional Solvent Extraction," Chemical Engineering Journal and the Biochemical Engineering Journal, vol. 61, No. 3, Mar. 1996, pp. 227-231.
Dunford et al., "Nutritional Components of Supercritical Carbon Dioxide Extracted Wheat Germ Oil," 6th Symposium on Supercritical Fluids, Retrieved from the Internet: http://www.ensic.inpl-nancy.fr/ISASF/Docs/Versailles/Papers/PN37.pdf, Apr. 2003, 6 pages.
The EFSA Journal (2005) 278, "Opinion of Scientific Panel on Dietetic Products, Nutrition and Allergies on a Request from the Commission Related to the Safety of Chia (*Salvia hispanica* L.) Seed and Ground Whole Chia Seed as a Novel Food Ingredient Intended for Use in Bread," http://www.efsa.eu.int/science/nda/nda_opinions/catindex_en.html, Oct. 5, 2005, pp. 1 12.
Laurange, "Agua Fresca De Chia" (Online) Aug. 30, 2007, XP002515363, Retrieved form the Internet: URL: http://www.saveursmexicaines.com/templates/home.php?page=86&content=128&;Ing=fr, 2 pages.
"Supercritical Chia Seed Oil Could Become Leading Source of Omega-3 Linolenic Acid" (Online) Nov. 30, 2005, XP002515364, Retrieved from the Internet: http://www.scientistilive.com/European-Food-Scientist/Ingredients/Supercritical_Chia_Seed_Oil_could_become_leading_source_of_omega-3_linolenic_acid/14463, 4 pages.
"Chia Semen CO2-to Extrakt" (Online) Jul. 7, 2005, Rehlingen, De, Retrieved from the Internet: URL:http://www.flavex.com/hmd.html, 1 page.
Viable Herbal Solutions (www.web.archive.org/web/20000124113842/http:/viable-herbal.com/herbology 1/herbs42htm, Copyrighted 1996, 1997, 1998 and 2000), pp. 1-3.
Flavex Naturextrakte (CO2 Extracts, Parfums Cosmetiques Actualities, 2007, 193, Feb./Mar. 2007, English Abstract, 1 page.
"Deep extract supercritical CO2 extraction", May 2009, pp. 1-3.
"Stabilization-O2B peroxidation blocker system", Sep. 2011, pp. 1-3.
"Defatting technology", Sep. 2011, pp. 1-2.
"Extraction technology—the case for supercritical CO2", Sep. 2011, pp. 1-4.
"Perilla seed oil—supercritical CO2 extract", May 2012, pp. 1-4.
Kim et al., "Supercritical carbon dioxide extraction of perilla seed oil", Foods and Biotechnology, Korean Society of Food Science and Technology, vol. 5, No. 4, Jan. 1996, pp. 300-304.
Guerin et al. "Haematococcus Astaxanthin: Applications for Human Health and Nutrition" Http:/tibtec.trends.com vol. 21 No. 5 May 2003 pp. 210-215.
Kagen et al. "Acute Appearance of Fatty Acids in Human Plasma—A Comparative Study Between Polar-Lipid Rich Oil from the Microalgae Nannochloropis Oculata in Krill Oil in Healthy Young Males," as published in Lipids in Health and Disease, 2013, 12:102.
Goldberg et al., "Biosynthesis of Eicosapentaenoic Acid (EPA) in the Fresh Water Eustigmatophyte *Monodus subterraneus* (Eustigmatophyceae)," J. Phycol, 38, 745-756 (2002).
Gavio et al. "*Grateloupia turuturu* (Halymeniaceae, Rhodophyta) is the Correct Name of the Non-Native Species in the Atlantic Known as *Grateloupia doryphora*," Eur. J. Phycol. (2002), 37: 349-359.

\* cited by examiner

EYE HEALTH COMPOSITION AND METHOD USING PLANT DERIVED SEED EXTRACT RICH IN ESSENTIAL FATTY ACIDS DERIVED FROM PERILLA SEED AND CAROTENOIDS

RELATED APPLICATION(S)

This is a continuation-in-part application of application Ser. No. 13/231,131 filed Sep. 13, 2011, which is a continuation-in-part application of application Ser. No. 12/419,321 filed Apr. 7, 2009 (now U.S. Pat. No. 8,586,104), which is based upon provisional application Ser. No. 61/043,773 filed Apr. 10, 2008, the disclosures which are hereby incorporated by reference in their entirety.

FIELD OF THE INVENTION

This invention relates to seed oil extracts and carotenoids used for eye care or other medical applications.

BACKGROUND OF THE INVENTION

It is well known in the literature that Polyunsaturated Fatty Acids (PUFAs) of all types are highly susceptible to peroxide, free radical and light induced degradation including rancification and polymerization making them unsuitable for human consumption. For example, it is well known that flax seed oil, also known as linseed oil, readily undergoes free radical oxidation to advantageously form polymeric surfaces including oil based paints, hard furniture finishes and linoleum flooring. In addition, many companies offer flax seed oil for human consumption as a dietary supplement or food ingredient because of the high levels of PUFAs found in raw flax seed and its expeller pressed oils and more particularly Alpha-Linolenic Acid (ALA) and Linolenic Acid (LA). Many flax seed oil product labels suggest that the product must be refrigerated at all times due to the instability of such PUFAs in flax seed oil. Careful examination of the majority of commercially available flax seed oils obtained by expeller pressing, including those typically stored under refrigerated conditions, unfortunately reveals that they are unfit for human use based on their measured Peroxide Values (PVs). Such PV values above 3 meq/Kg (milliequivalents/gram) are deemed not suitable for salad oil applications and PV values above 10 meq/Kg are deemed to be unsuitable for human use because the measured PV value may be an early indicator of rancidity and free radical induced degradation. On the other hand, PV values taken alone do not adequately characterize such oils since a low PV value can also be associated with PUFA's that have already gone through the rancification process. Typical testing has revealed flax seed oil products sold for human consumption with observed PV's as high as 130 meq/kg also characterized with the odor associated with short chain aldehydes that make such oils "rancid" to olefactory senses.

Most raw seed based oils in common cooking and baking use, such as soybean, corn and canola seed oils naturally contain enough PUFAs making them unsuitable, without further processing, for use as cooking oils. Therefore unless such PUFA containing raw seed oils are hydrogenated to fully saturated triglycerides using hydrogen and a catalyst prior to their use in cooking applications, they are considered to be unfit for use as cooking oils. These oils are typically first isolated by, for example, expeller pressing the appropriate seed. The crude seed oil is then filtered to remove biomass. The resulting oil, containing significant levels of PUFAs, is then catalytically hydrogenated to reduce the PUFA content to levels suitable for use of the resulting oil in cooking applications. If the hydrogenation process is incomplete, however, the resulting mixtures are found to contain both undesirable heat labile PUFAs that quickly undergo rancification to small chain aldehydes in the resulting heated cooking oil as well as unsaturated trans-fatty acids which are believed to be detrimental to animal and especially human health.

Therefore, those skilled in the art will recognize the great difficulty in producing a shelf stable PUFA mixture wherein the PUFA content is as high as 70% wt/wt of the resulting seed extract from a natural seed source that then exhibits extraordinary room temperature stability.

Commonly assigned and copending patent application Ser. No. 13/231,131, filed Sep. 13, 2011, discloses a *perilla* seed oil extract that provides a healthy source of omega-3 and contains a very favourable ratio of ALA to LA (omega-3 to omega-6) of about 6:1 in one example. This *perilla* seed oil extract is obtained by pressing the *perilla* seeds to initiate seed cracking, processing the cracked biomass using supercritical $CO^2$ fluid extraction, and collecting the extract to deliver more of the higher molecular weight compounds.

Commonly assigned and copending patent application Ser. No. 13/553,025 filed Jul. 19, 2012, and Ser. No. 13/937,537 filed Jul. 9, 2013, the disclosures which are hereby incorporated by reference in their entirety, disclose compositions and methods that enhance eye health, treat eye disorders, retard and ameliorate eye diseases and injuries, enhance other medical conditions such as cardiovascular health. The compositions include a mixture of carotenoids, including astaxanthin with phospholipid and triglyceride bound EPA and DHA derived from krill oil, in which the krill oil contains at least 30% total phospholipids and in a therapeutically effective amount to prevent, retard or treat eye and central nervous system diseases or injuries, such as age-related macular degeneration, cataract, dry eye syndrome due to glandular inflammation and other central nervous system degenerative diseases, photic injury, ischemic diseases, and inflammatory diseases, including related to the cardiovascular system. Krill oil is the oil based composition as used but other oils can be used. It is desirable, however, to use a *perilla* seed oil extract for eye health and related cardiovascular applications and take advantage of the benefits of various carotenoids.

SUMMARY OF THE INVENTION

A dietary supplement composition is formulated in a therapeutically effective amount to treat the eye of an individual. The composition includes a *perilla* seed oil extract, astaxanthin, and at least one carotenoid selected from the group consisting of lutein, trans-zeaxanthin and meso-zeaxanthin.

The composition in one example includes 0.5 to 8 mg of astaxanthin, 2 to 15 mg of lutein, and 0.2 to 12 mg of trans-zeaxanthin on a daily basis. In another example, the composition includes about 4 mg of astaxanthin, about 10 mg of lutein, and about 1.2 mg of trans-zeaxanthin. The composition may also include about 50 to 500 mg of *perilla* seed oil extract on a daily basis.

In another example, the dietary supplement composition is formulated into single dosage capsules. The astaxanthin is formed from 3S,3'S-astaxanthin derived from *Haematococcus pluvialis*. In an example, the 3S,3'S-astaxanthin is 0.1 to 16% by weight of the *perilla* seed oil extract, and the lutein is 0.4 to 30% by weight of the *perilla* seed oil extract, and the trans-zeaxanthin is 0.04 to 24% by weight of the *perilla* seed oil extract in an oral dosage form. It is possible to supplement the *perilla* seed oil extract with krill and/or algae based oil.

In another example, the *perilla* seed oil extract is formed as a shelf stable, supercritical CO2 fluid extracted seed oil derived from a cracked biomass of *perilla frutescens*. In an example, the *perilla* seed oil extract includes from about 0 to 95% w/w of PUFA's in a ratio of from about 4:1 to about 6:1 alpha-linolenic acid (ALA) to linoleic acid (LA). The peroxide value of the *perilla* seed oil extract is under 10.0 MEQ/KM.

A method aspect is also disclosed for treating the eye of an individual by administrating in an oral dosage form a therapeutically effective amount of a dietary supplement composition that is formed by the *perilla* seed oil extract, astaxanthin, and at least one carotenoid selected from the group consisting of lutein, trans-zeaxanthin, and meso-zeaxanthin.

BRIEF DESCRIPTION OF THE DRAWINGS

Other objects, features and advantages of the present invention will become apparent from the detailed description of the invention which follows, when considered in light of the accompanying drawings in which.

DETAILED DESCRIPTION OF THE PREFERRED EMBODIMENTS

Figure 1:
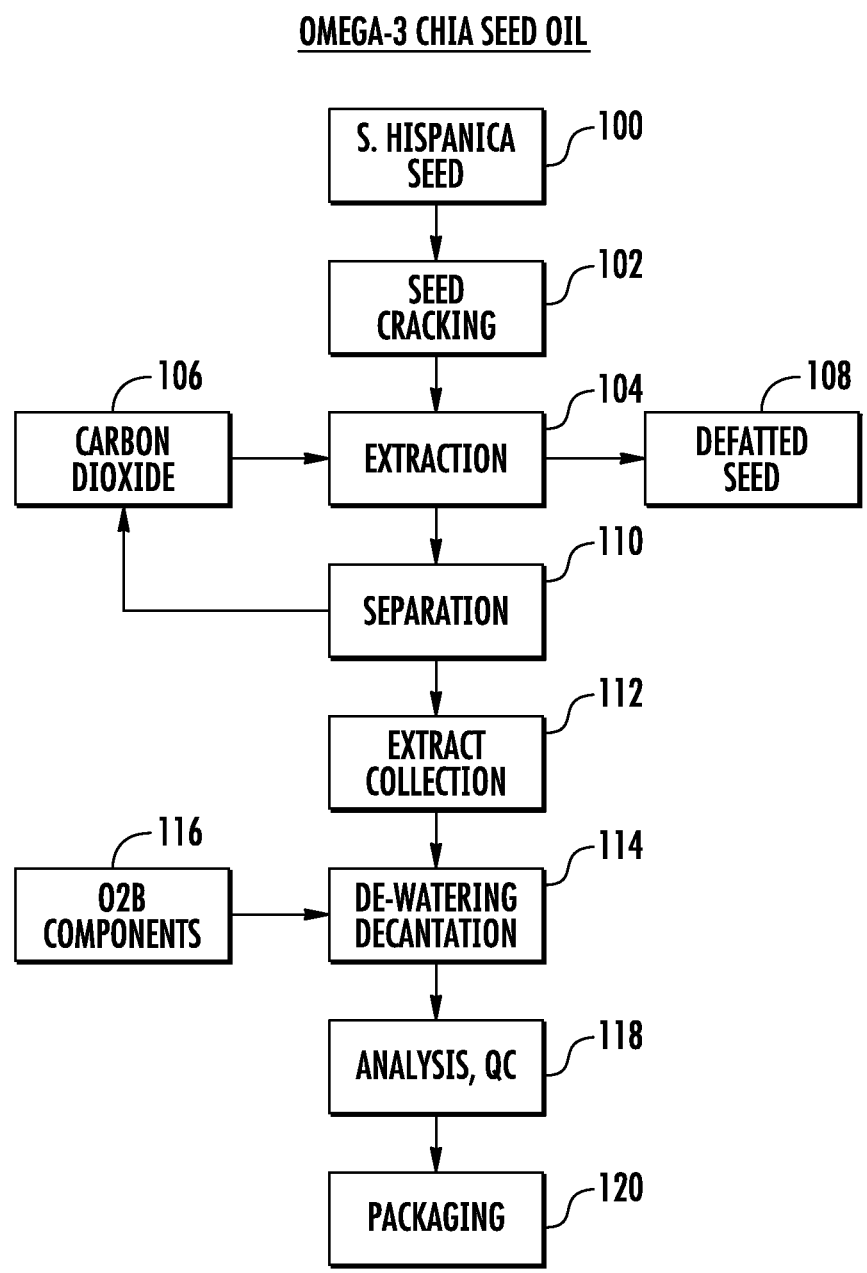
FIG. 1 is a flowchart illustrating a production diagram as a flowchart for producing omega-3 chia seed oil such as sold under the tradename Chia Gold™ by Valensa International of Eustis, Fla.

The present invention will now be described more fully hereinafter. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The *perilla* seed oil extract and mixed carotenoids includes astaxanthin, including S,S'-astaxanthin derived from *Haematococcus pluvialis* and one or more of lutein and/or trans-zeaxanthin or meso-zeaxanthin to provide an eye health care composition and method that retards and ameliorates eye diseases and injuries and prevents, retards or treats eye and central nervous system diseases or injuries, including age-related macular degeneration, cataract, dry eye syndrome due to glandular inflammation and other central nervous system degenerative diseases, photic injury, ischemic diseases, and inflammatory diseases, including cardiovascular.

There now follows a description of the parent and grandparent applications as directed to forming an oil extract such as supercritical fluid CO2 solvent extracted oil from respective premilled *salvia hispanica* L. seed or *perilla* seed oil extract.

Commonly assigned and copending grandparent application Ser. No. 12/419,321 discloses a room temperature, shelf stable mixture of an approximate 3.1:1 to about 3.3:1 mixture of alpha-linolenic acid ("ALA", "Omega-3 polyunsaturated fatty acid" ("PUFA")) to linoleic acid ("LA", "Omega-6 PUFA) that has been prepared in the presence of limited amounts of saturated and mono-unsaturated fatty acids as their mixed triglycerides by the use of either supercritical fluid $CO^2$ solvent extraction of premilled *Salvia hispanica* L. seed alone, and more particularly, supercritical fluid $CO^2$ solvent extraction in the presence of mixtures of hydrophilic and lipophilic antioxidants, or, by the use of a common organic solvent extraction such as hexane or by the use of expeller pressing techniques. The supercritical $CO^2$ extraction is preferred.

Such Omega-3 and Omega-6 PUFAs are well known as essential fatty acids in man and many animals, which are useful in humans and animals in promoting, for example, a heart healthy condition in man. It is also well known, however, that PUFAs are extremely susceptible to rapid, uncontrollable free radical mediated degradation.

The composition of matter disclosed in the copending '321 application includes a supercritical $CO^2$ *Salvia hispanica* L. derived seed oil comprising from 60-88% PUFAs in a ratio of from about 3.1:1-3.3:1 of alpha-linolenic acid (ALA) to linoleic acid (LA), 4-10% of C-18 mono-unsaturated fatty acid, 1-5% of C-18 saturated fatty acid and 4-8% of C-16 saturated fatty acid in a mixed triglyceride form that is stable at room temperature for 12-24 months and comprising a mixture of selected antioxidants.

The composition of matter includes dietary supplement ingredients such as docosahexaenoic acid (DHA) and/or eicosapentaenoic acid (EPA) in pectin or gelatin based confectionary dietary supplement delivery systems. EPA, DHA, docosahexaenoic acid (DPA) or gamma-linlolenic acid (GLA), fish oil, krill oil, krill oil concentrate, borage oil, evening primrose oil, olive oil or other plant, animal or algal based seed or fruit oils are admixed therein either alone or in combination. Lipophilic antioxidants are added either alone or in combination with at least one of a) phenolic antioxidants including at least one of sage, oregano, and rosemary; b) tocopherol, c) tocotrienol(s), d) carotenoids including at least one of astaxanthin, lutein, and zeaxanthin; e) ascorbylacetate; f) ascorbylpalmitate g) Butylated hydroxytoluene (BHT); h) Docosapentaenoic Acid (BHA) and i) Tertiary Butyl hydroquinone (TBHQ). As disclosed, a hydrophilic antioxidant or sequesterant includes hydrophilic phenolic antioxidants including at least one of grape seed extract, tea extracts, ascorbic acid, citric acid, tartaric acid, and malic acid. These ingredients can be used with the *perilla* seed oil extract.

As further disclosed in this incorporated by reference '321 application, this PUFA rich seed oil extract is prepared from *Salvia hispanica* L. seed which contains one of nature's more favorable seed based concentrations and ratios for the essential fatty acids, and more specifically, the essential fatty acids ALA and LA in a ratio of approximately 3.3:1 as a mixture of ALA and LA that is stable at room temperature for long periods of time when desirably and appropriately treated with antioxidants either before, during, or after (or any combination thereof). A shelf life of 12-24 months has been found.

Such oils, including the Chia and *perilla* seed oil extracts, are used either alone or advantageously in combination with other ingredients, for example, algae, plant or fish oil derived alpha-linolenic acid (ALA) or linoleic acid (LA) metabolites such as eicosapentaenoic acid (EPA), docosapentaenoic acid (DPA), gamma-linlolenic acid (GLA) or docosahexaenoic acid (DHA) or any combination thereof, incorporated into appropriate foods, beverages or dietary supplements for the prevention or mitigation of such diseases as cardiovascular disease, arthritis, pain, blood clotting, dry eyes and brain health.

Such disease mitigation has been associated with the competitive control of the LA metabolic cascade and the resulting metabolic cascade products from LA metabolism known commonly as eicosanoids, such as the series 2 and 3 prostaglandins and thromboxanes, the series 4 leuotrienes and lipoxins and the series 5 leuotrienes all of which are potent platelet aggregators and/or inhibitors, pro-inflammatories, vasodilators, bronchoconstrictors, or anti-asthmatics and the like.

The consumption of ALA has been shown to be a very effective competitive substrate of delta-6 desaturase, which is known to be the rate limiting enzymatic step in both ALA and LA metabolism to the metabolic products discussed above.

Attempted extraction of *Salvia hispanica* L. (and *perilla*) unmilled seed, using supercritical $CO^2$ even at extraordinarily high pressures of 1000 bar or hexane solvent at atmospheric pressures, yields very little, if any, seed oil, therefore the seed must be milled prior to extraction. The extent of the milling, as measured by particle size distribution, is advantageous to the extraction process in accordance with a non-limiting aspect since the higher the surface area, the higher will be the efficiency and completeness of the extraction process by either organic solvent based or supercritical fluid based processes. In addition, it is often advantageous to mill the seed in a blanket of inert gas such as nitrogen to prevent per-oxidative processes from taking place that would otherwise be initiated in the presence of air or oxygen and light.

In one embodiment, *Salvia Hispanica* L. whole seed is either first commutated in a standard knife or hammer mill or more preferably roller milled, preferably under a cold nitrogen atmosphere, to produce a cracked seed biomass. The seed biomass is preferably treated with one or more hydrophilic and/or lipophilic antioxidants by mixing the antioxidants to the resulting biomass. In another embodiment, the antioxidant may be advantageously added to the seed prior to or during the milling process or at the point of extraction without pre-blending the antioxidants evenly throughout the resulting biomass due to the nature of the extraction process. The biomass is then transferred to a supercritical fluid extraction unit for separation of the seed oil from the cracked or flake-rolled biomass.

Alternatively, the pre-prepared biomass can be transferred to a common hexane solvent extractor, or an expeller press for example, and the oil extracted from the biomass accordingly. Preferably either process is conducted in the absence of oxygen or air.

The supercritical fluid extraction of the milled seed admixed with hydrophilic and/or lipophilic antioxidants is accomplished by subjecting the premilled cracked or flake-rolled seed to supercritical $CO^2$, or $CO^2$ and propane as a co-solvent, or supercritical propane alone at from 40-1000 bar at from 30-100 Deg. C. More preferably the seed oil is extracted from the biomass between 50-800 bar at 50-90 deg. C. in such $CO^2$ amounts measured in kgs/kg of biomass and for such times as may be required to extract large portions of the seed oil content from the biomass. In addition, entrainment solvents can be added to the supercritical fluid to further enhance the efficacy of such extractions. For example, supercritical carbon dioxide extraction of the biomass can be enhanced by the addition of propane to the supercritical extraction fluid.

The resulting seed oil dissolved in supercritical solvent(s) is next allowed to fractionate in two separate pressure step-down stages allowing the collection of a light and heavy fraction of seed oil extract. This light fraction also contains water that has been co-extracted from the seed mass. The resulting seed oil, after degassing, is separated from any water that may have been carried over during the extraction of the biomass containing the water. The light fraction of the seed oil extract is rich in taste and odor components and may be admixed with the heavy fraction or may be discarded depending on the desired product characteristics.

After separation of the water remaining in each fraction, the fractions are then held under nitrogen or other inert gas and additional amounts of lipophilic and/or hydrophilic antioxidants may then be added. In addition, the resulting fractions may also be treated with bleaching clay, carbon and such other processing aids as may be required to render the oil suitable for its intended use in humans and animals.

The PV of the resulting seed oil extract is typically under 2.0 meq/Km, while accelerated decomposition, using a Rancimat instrument, remarkably indicates an extrapolated room temperature shelf life of from about 1-2 years. When the same process is repeated without the use of antioxidants, the resulting PV is surprisingly under 10.0 meq/Kg most probably due to the use of supercritical $CO^2$ resulting in minimal exposure of the oil to oxygen species. However, the resulting oil quickly begins to build peroxide value in the presence of air even when stored at temperatures of 0 Degs. C. In addition, such unstabilized oils, under accelerated rancimat testing exhibit very poor stability to heat and oxygen unlike the rancimat performance observed in stabilized oils derived from the process described above.

The resulting supercritical fluid seed oil extract contains from 60-88% PUFAs in a ratio of from 3.1:1-3.3:1 of ALA:LA, 4-10% of C18 mono-unsaturated fatty acid, 1-5% of C-18 saturated fatty acid and 4-8% C-16 saturated fatty acid composition in a mixed triglyceride form depending on the seed source employed.

On the other hand, if the process described above is conducted without the use of hydrophilic and/or lipophilic antioxidants, the resulting seed oil extract exhibits an initial low PV but accelerated stability testing using a Rancimat instrument indicates an extrapolated room temperature shelf stability of less than two months.

The stability of the resulting oil at room temperature that is manufactured without the use of added antioxidants cannot be easily explained because of the available levels of the powerful natural antioxidants found in *Salvia hispanica* L. whole seed whose activity can be easily measured in Oxygen Radical Absorbance Capacity (ORAC) units. *Salvia hispanica* L. has a measured ORAC number of 3000 micromoles TE ORAC units/gram of seed and is known to contain such antioxidants as myricetin, quercetin, kaempferol, caffeic acid, and chlorogenic acid. In addition, it is well known that the *Salvia hispanica* L. whole seed, unlike many other seeds bearing PUFA containing oil, exhibits a shelf life of at least 5 years due to its structure and the naturally occurring antioxidants available in the seed matrix.

In addition, cold pressing of *Salvia hispanica* L. whole seed also produces unstable seed oil without careful addition of appropriate antioxidants to the seed prior to the expeller pressing process.

In a non-limiting example the composition of matter is formed from a supercritical $CO^2$ derived *Salvia hispanica* L. derived seed oil comprising from 60-88% PUFAs in a ratio of from 3.1:1-3.3:1 of alpha-linolenic acid (ALA) to linoleic acid (LA), 4-10% of C-18 mono-unsaturated fatty acid, 1-5% of C-18 saturated fatty acid and 4-8% of C-16 saturated fatty acid in a mixed triglyceride form that is stable at room temperature for 12-24 months and comprising a mixture of selected antioxidants.

It includes docosahexaenoic acid (DHA) and/or eicosapentaenoic acid (EPA) in pectin or gelatin based confectionary dietary supplement delivery systems and in another aspect EPA, DHA, docosapentaenoic acid (DPA) or gamma-linolenic acid (GLA), fish oil, krill oil, krill oil concentrate, borage oil, evening primrose oil, olive oil or other plant, animal or algal based seed or fruit oils are admixed therein.

Lipophilic antioxidants are added either alone or in combination with at least one of a) phenolic antioxidants including at least one of sage, oregano, and rosemary; b) tocopherol, c) tocotrienol(s), d) carotenoids including at least one of astaxanthin, lutein, and zeaxanthin; e) ascorbylacetate; f) ascorbylpalmitate g) Butylated hydroxytoluene (BHT); h) Docosapentaenoic Acid (BHA) and i) Tertiary Butyl hydroquinone (TBHQ). The hydrophilic antioxidant or sequesterant includes hydrophilic phenolic antioxidants including at least one of grape seed extract, tea extracts, ascorbic acid, citric acid, tartaric acid, and malic acid in another aspect.

A method of manufacturing a *Salvia hispanica* L. derived seed oil in another non-limiting example is set forth. The seed oil comprises from 60-88% PUFAs in a ratio of from 3.1:1-3.3:1 of alpha-linolenic acid (ALA) to linoleic acid (LA), 4-10% of C-18 mono-unsaturated fatty acid, 1-5% of C-18 saturated fatty acid and 4-8% of C-16 saturated fatty acid in a mixed triglyceride form that is stable at room temperature for 12-24 months and includes antioxidants. The method includes milling or roller press flaking *Salvia hispanica* L. seed in the absence of oxygen to obtain a desired particle size distribution with or without the addition of hydrophilic or lipophilic antioxidants during the particle sizing process. The resulting biomass is subjected to supercritical fluid $CO^2$ extraction in the presence of lipophilic and/or hydrophilic antioxidants. Any resulting seed oil fractions are collected. The water is separated in each fraction.

Any resulting seed oil fractions can be treated with additional antioxidants to afford a desired room temperature stability. The extent of oil extraction can be controlled by particle size distribution of the milled or flaked seed. Propane can be added in mixture with supercritical $CO^2$ in the supercritical state as an extraction solvent. In yet another aspect solvent can be extracted using hexane extraction at or near atmospheric pressures and the resulting boiling point of hexane in the absence of oxygen, separating the resulting water from the oil/hexane mixture and removing the hexane solvent by distillation at or below atmospheric pressure in the absence of oxygen.

Lipophilic antioxidants can be added to increase the room temperature stability of the resulting oil. The lipophilic antioxidants can be added either alone or in combination with at least one of a) phenolic antioxidants including at least one of sage, oregano, and rosemary; b) tocopherol, c) tocotrienol(s), d) carotenoids including at least one of astaxanthin, lutein, and zeaxanthin; e) ascorbylacetate; f) ascorbylpalmitate g) Butylated hydroxytoluene (BHT); h) Docosapentaenoic Acid (BHA) and i) Tertiary Butyl hydroquinone (TBHQ). The resulting dewatered seed oil can be treated with bleaching clay or activated carbon.

Premilled or roller press flaked seed can be treated with a lipophilic or hydrophilic antioxidant(s) prior to solvent extraction. The hydrophilic antioxidant or sequesterant can be formed from hydrophilic phenolic antioxidants including at least one of grape seed extract, tea extracts, ascorbic acid, citric acid, tartaric acid, and malic acid.

A method of mitigating or preventing cardiovascular disease, arthritic pain and inflammation, platelet aggregation, or treating dry eye syndrome, premenstrual symptoms or modifying immune response in humans or animals is set forth by applying an effective amount of a dietary supplement, food or beverage to which has been a composition mixed therewith and comprising a *Salvia hispanica* L. derived seed oil comprising from 60-88% PUFAs in a ratio of from 3.1:1-3.3:1 of alpha-linolenic acid (ALA) to linoleic acid (LA), 4-10% of C-18 mono-unsaturated fatty acid, 1-5% of C-18 saturated fatty acid and 4-8% of C-16 saturated fatty acid in a mixed triglyceride form that is stable at room temperature for 12-24 months and includes antioxidants.

In one aspect, an emulsifying agent is added. In another aspect, nano- and/or micro-particles of rice or sugarcane based polycosanol are dispersed for enhancing a heart healthy dietary supplement. A stabilized oil in a fruit juice concentrate, fruit puree or other water based flavoring is dispersed in the presence of maltodextrin, or other carbohydrates, and a suitable emulsifying or emulsion stabilization agent that is vacuum spray dried to form an amorphous or crystalline solid suitable for use as a flavoring ingredient carrying stabilized PUFAs in flavored dietary supplements, foods and beverages. In yet another aspect, oil based flavors and fragrances suitable for use as an ingredient in foods, beverages and cosmetics are added. ALA and LA are also added as essential fatty acids.

As noted before, it has also been found that the use of a *perilla* seed oil extract instead of the disclosed chia seed oil is advantageous and contains a very favorable ratio of ALA to LA (omega-3 to omega-6) of as high as about 6:1 in some examples as compared to chia seed oil that is typically about 3.3:1 ALA to LA. *Perilla* seed oil extract as obtained, in accordance with a non-limiting example, in a similar manner as described relative to the preparation and extraction of the chia seed oil. It has been found, however, that the *perilla* seed oil extract is an even healthier source of omega-3 than chia seed oil in some non-limiting examples.

FIG. 1 is a flowchart showing a production diagram for a sequence of steps for producing omega-3 chia seed oil such as sold under the tradename Chia Gold™ by Valensa International of Eustis, Fla. The *salvia hispanica* seed is provided (block 100) and seed cracking occurs (block 102) to form a cracked biomass. Various techniques for seed cracking and forming the biomass can be used as described above. The supercritical $CO^2$ extraction (block 104) uses ultra high pressure carbon dioxide extraction technology and supplied $CO^2$ (block 106) such as the DEEP EXTRACT® manufacturing process developed by Valensa International of Eustis, Fla. The defatted seed as a flour, for example, (block 108) is produced. Separation of the different portions occurs such as by fractionating the seed oil extract (block 110) as described above. The extract is collected (block 112). Dewatering and decantation occurs (block 114) and antioxidants are added (block 116) such as the OTB® Per Oxidation blocker system from Valensa International. Quality control analysis occurs (block 118) and the final oil packaged (block 120).

Figure 2:
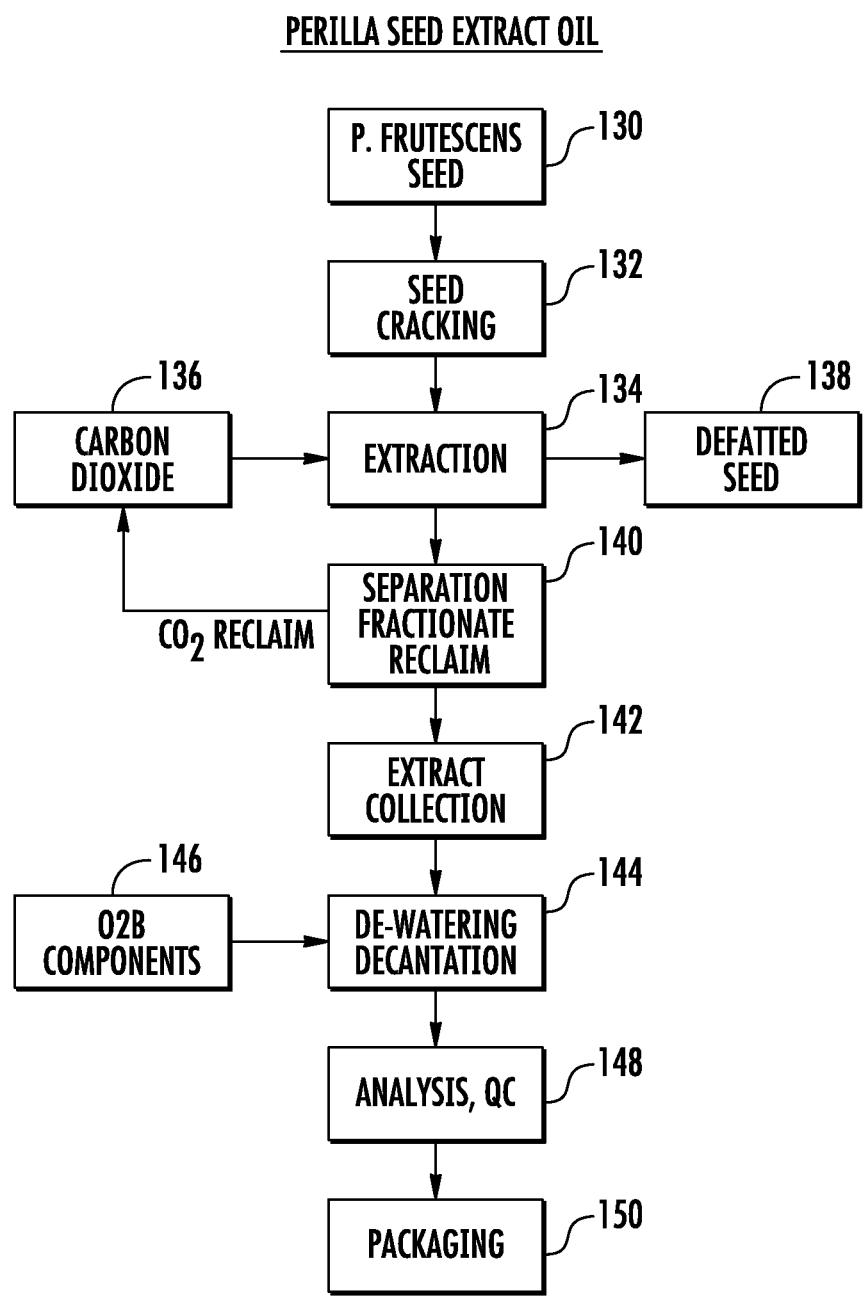
FIG. 2 is another production diagram as a flowchart showing basic steps for manufacturing a *perilla* seed oil extract in accordance with a non-limiting example.

FIG. 2 shows a second production diagram as a flowchart for producing the *perilla* seed oil extract in accordance with a non-limiting example. The process begins with a source of the *perilla* seed also known as *perilla frutescens* seed (block 130). Similar to the process with the omega-3 chia seed oil, seed cracking occurs (block 132) to form a cracked seed biomass followed by the extraction (block 134) using the supercritical $CO^2$ extraction and supplying carbon dioxide (block 136) to produce the defatted seed (block 138) that is partially or wholly defatted *perilla* seed as a cake residue with virtually no fat or oil. The other portion is the oil is separated and the $CO^2$ is reclaimed (block 140). Similar to the omega-3 chia seed oil, the extract is collected (block 142) and dewatering and decantation occurs (block 144). Antioxidants such as the OTB® components as described before are added (block 146) and the quality control analysis occurs (block 148) followed by packaging (block 150).

It should be understood that the *perilla* seed oil extract can be supercritically extracted in a similar process as used with the chia seed as described above. For example, the resulting seed oil with the *perilla* seed extract is allowed to fractionate after supercritical solvent extraction in two separate pressure step-down stages allowing the collection of a light and heavy fraction of seed oil extract. The similar process and temperatures such as extraction from the biomass between 50-800 bar at 50-90 degrees C. and such CO2 amounts measured in KGS/KG of biomass may be used as also described above. It is possible to use propane as a co-solvent or supercritical propane alone at from 40-1,000 bar from 30-100 degrees C.

The *perilla* seed oil extract can have a range of values for its fatty acid profile depending on the quality and type of seed cracking and extraction parameters. Total fatty acids, peroxide values and other component values are described in Table 1 below showing an analysis of *perilla* seed extract and various parameters, specifications and results as a non-limiting example. Results can vary of course for different samples.

TABLE 1

Ingredients:
Perilla (*Perilla frutescens* (L) Britton) Seed Oil, O2B ™ Botanical peroxidation blocker including refined nonGMO soybean mixed tocopherols and spice extract.

| Parameter | Specification | | Result |
|---|---|---|---|
| Description | Clear yellow oil, pourable at room temperature | | Conforms |
| Odor | Mild | | Conforms |
| Solubility | Insoluble in water, miscible with oils | | Conforms |
| Fatty Acid Profile (%) | VQP-050 (GC) | | |
| Palmitic Acid | | | 6.3 |
| Stearic Acid | | | 1.9 |
| Oleic Acid | | | 22.3 |
| Linoleic Add | | | 9.7 |
| α-Linolenic Acid | >56 | | 59.8 |
| Total Fatty Acids (% w/w) | 85 . . . 95 | | 88.6 |
| Peroxide Value (meqO$_2$/kg) | <10 | VQP-049 | 2.3 |
| Water Content (%) | <1.5 | VQP-048 | <0.2 |
| Heavy Metals (ppm) | <10 | ICP-MS | <1 |
| Microbiological Data (cfu/g) | | | |
| Total Aerobic Microbial Count | <10$^3$ | USP <61> | <100 |
| Combined Yeast & Mold | <10$^2$ | USP <61> | <100 |
| E. coli/Total Coliforms | <10 | AOAC 991.14 | <10 |

{all values as is basis}
All of the ingredients are GMO free. Therefore this product is in accordance with EU regulations 1830/2003 and 1829/2003. The Product has not been treated with gamma rays.

Table 2 show accelerated stability testing of the *perilla* seed extract with an OTB® per oxidation blocker and Table 3 shows the accelerated stability testing of a *perilla* seed extract sample produced by Valensa International of Eustis, Fla. as compared to chia seed extracts such as the Chia Gold™ which is produced by the process shown in FIG. 1.

TABLE 2

Accelerated Stability Testing of Valensa
*Perilla* Seed Extract with O2B ®

| | Rancidity Induction Time (hr)[1] | Shelf Life @20° C. (yr)[2] |
|---|---|---|
| *Perilla* Oil (without O2B) | 7 | 0.5 |
| *Perilla* Oil (with O2B) | 42 | 2.8 |

[1]Rancimat induction time measured in hours with air bubbling through heated oil (90° C.) in the light.
[2]Rancimat data is a function of accelerated high heat and oxygen exposure. Extrapolated data plots are assumed linear in the presence of air and light at 20° C. however, if product is stored at 20° C. in an air and light barrier package, then shelf stability is at least doubled.

TABLE 3

Accelerated Stability Testing of Valensa *Perilla*
Seed and Chia Seed Extracts with O2B ®

| | Rancidity Induction Time (hr)[1] | Shelf Life @20° C. (yr)[2] | Shelf Life Increase (%) |
|---|---|---|---|
| *Perilla* Oil (without O2B) | 7 | 0.5 | |
| *Perilla* Oil (with O2B) | 42 | 2.8 | 611% |
| Tresalbio Chia Oil (without O2B) | 12 | 0.4 | |
| Tresalbio Chia Oil (with O2B) | 73 | 2.2 | 603% |
| ChiaGold Oil (without O2B) | 9 | 0.3 | |
| ChiaGold Oil (with O2B) | 60 | 1.8 | 663% |

[1]Rancimat induction time measured in hours with air bubbling through heated oil (80-90° C.) in the light.
[2]Rancimat data is a function of accelerated high heat and oxygen exposure. Extrapolated data plots are assumed linear in the presence of air and light at 20° C. however, if product is stored at 20° C. in an air and light barrier package, then shelf stability is at least doubled.

Table 1 illustrates various values and shows the total fatty acids (% w/w) is 85 to about 95 and has in that particular example a result of 88.6. It should be understood that the seed oil could possibly have as low as about 60% w/w of PUFAs and as high as about 95% and a ratio of from about 4:1 to about 6:1 ALA to LA. The peroxide value of the seed oil is typically under 10.0 meq/Km. The PUFAs typically comprise at least greater than 50% ALA and in the example shown in Table 1 is greater than 56% and in one particular example shown in FIG. 1 is 59.8. The seed oil is shelf stable at room temperature up to 32 months in a particular example. Other data is shown such as specific components of the fatty acids and the water content, heavy metals in PPM, and microbiological data in CFU/G, such as the total aerobic microbial count, a combined yeast and mold and *E. coli*/total coliforms. All the values are an as-is basis and the ingredients are GMO free. Therefore, this product is in accordance with EU regulations 1830/2003 and 1829/2003. This product had not been treated with gamma rays. Ingredients include the *perilla* (*perilla frutescens* (L) Britton) seed oil, OTB® botanical per oxidation blocker including refined non-GMO soybean mixed tocopherols and spice extracts. GMO corresponds to genetically modified organisms, and thus, non-GMO refers to non-genetically modified organisms. The soybean had not been created through gene-splicing techniques of biotechnology or genetic engineering.

The production diagram in FIG. 2 shows the process used to obtain the *perilla* seed extract in accordance with a non-limiting example. The extraction technology has been described relative to the Chia seed oil and extract in the incorporated by reference parent application and described above in some detail. Similar processing parameters may be used. It should be understood that extraction technology creates materials for human nutrition and supplementation and offers various benefits including enhanced efficacy with the isolation of key components to allow higher dosage and targeted performance. Extraction allows standardization. Natural materials tend to vary in make-up and extraction makes them consistent. It is also convenient because smaller dosages of high efficiency materials allow a consumer to more easily obtain the required levels of nutrients in a daily regimen. There is also enhanced safety because extraction gives more of the desired products and less of what is not desired. Extraction allows the removal of compounds that are not optimal for human health from natural materials.

The desired extraction technology uses the DEEP EXTRACT® process from Valensa International as an ultra high pressure carbon dioxide extraction technology that yields micronutrients and has high extraction efficiency to deliver more of the higher molecular weight compounds that more closely track the natural source materials. The process is flexible and allows for possible fractionation of the product if desired and delivery of specific compounds out of the raw material.

This extraction process, such as the DEEP EXTRACT® process, offers a more gentle treatment of high value raw materials at temperature levels that are substantially below those used in other expeller press processes and some chemical solvent extraction processes in the absence of oxygen. This reduces the degradation of liable compounds, chemical change of a component and the oxidation potential. The supercritical $CO^2$ process offers virtual sterilization of the finished product and biomass, which are untouched by chemical solvents and stay "natural" as before extraction. Selective fractionation as described above is advantageous. Pressure is a main tool used to tailor the resulting fractionated products for chia or *perilla* for product quality and efficient manufacturing. Because the $CO^2$ extraction is an all-natural and organic process, the final product is devoid of impurities and residues and delivers through the supercritical $CO^2$ extraction the high molecular weight compounds such as sterols, carotenoids and long chain alcohols.

Supercritical $CO^2$ extraction is advantageous over other methods used for extracting botanicals, including tinctures (usually alcohol extraction; steam distillation; expeller pressing, sometimes referred to as "cold pressing," and chemical solvent extraction). Chemical solvent extraction technology using strong solvents and supercritical $CO^2$ technology using high pressures typically offer the most comprehension extraction of a botanical. Supercritical $CO^2$ extraction conducted under very high pressure is advantageous. When carbon dioxide gas ($CO^2$) is compressed above 73 bar at a temperature above 31 degrees C. (87.8 degrees Fahrenheit), it transforms into a dense gas as supercritical $CO^2$, which has an extremely high solvating capacity and a power to extract constituents of botanicals. Its solvating capacity is a function of its density and by changing its density with pressure, the manufacturer is able to select the quality, quantity and specific principles of the targeted extract. Supercritical $CO^2$ is biologically compatible and generally regarded as safe (GRAS) by the FDA. It is also non-flammable and environmentally sound.

Any defatted cake resulting from the supercritical $CO^2$ process is typically viable and can be marketed or used for further processing in a wide range of human/food applications. Sometimes the defatted cake is the primary product and the oil is secondary as described in commonly assigned U.S. patent application Ser. No. 12/349,100 as filed on Jan. 6, 2009 and published as U.S. Patent Publication No. 2009/0181127, the disclosure which is hereby incorporated by reference in its entirety. That application describes a chia seed composition as a composition of matter formed from a stable, defatted whole grain flour derived from *salvia hispanica* L. whole ground seed using a suitable solvent such as using supercritical $CO^2$ fluid extraction. This chia seed extraction demonstrates that after processing of supercritical $CO^2$, the extract cake contains in some examples virtually no fat or oil and the resultant powder is approximately 50% protein and 50% carbohydrates that exist essentially as fiber.

The supercritical $CO^2$ process offers a gentle treatment of high value raw materials at temperature levels substantially below those used in expeller press in some chemical solvent extraction operations in the absence of oxygen. This reduces the degradation of labile compounds, chemical changing components and the oxidation potential. The supercritical $CO^2$ process offers virtual sterilization of the finished product and biomass that are untouched by chemical solvents and stay "natural" as they were before extraction. It also allows the advantage of fractionating the extracted components selectively with pressure tailoring the resulting fractionated products for product quality and efficient manufacturing. This addresses pesticide/insecticide residues and handle concerns about microorganisms that are present in expeller press materials.

The *perilla* seed oil extract as shown in FIG. 2 is dewatered and decanted and antioxidants added such as the Valensa OTB® per oxidation blocker system as a stabilizer to ensure that the botanical extract reaches a consumer in an efficacious and safe form. Stabilization with the OTB® components increases shelf life and continued product quality and is advantageous over using preservatives to stabilize natural materials, which is often seen as a negative by consumers. The OTB® per oxidation blocker system used by Valensa is 100% natural, non-GMO, and protects sensitive oils and particularly the highly unsaturated oils derived from fish and botanicals from the manufacture to consumption. The OTB® per oxidation blocker is a synergistic proprietary formulation of powerful natural compounds including astaxanthin, phenolic antioxidants and natural tocopherols. This technology prevents destructive oxidative, photochemical and rancification reactions. It protects expensive and sensitive compounds such as carotenoids and polyunsaturated fatty acids and can boost the effectiveness of other antioxidants such as vitamin E because it chemically quenches stable vitamin E free radicals. The antioxidants have in-vivo activity to protect both products and people.

*Perilla* has a number of essential oils. These are extracted from the leaves of *perilla*. About 50% to about 60% of perillaldehyde is responsible for so much of the aroma and taste of *perilla*. There are other terpenes such as limonene, caryophyllene and farnesene. There are other chemotypes such as *perilla* keytone (PK), esholzia keytone (EK), perillene (PL), and various phenylpropanoids such as myristicin, dillapiole and elemicin. Citral is a type rich in rosefuran. *Perilla* oil typically is obtained by pressing the seeds of *perilla* that contain about 35% to about 45% oil. In some parts of Asia, *perilla* oil is an edible oil valued for medicinal benefit. Typically, *perilla* oil is a rich source of omega-3 fatty acid alpha-linolenic acids. As a drying oil, it is similar to tong oil or linseed oil and is sometimes used in paint, varnish, linoleum, printing ink, lacquers and other protective waterproof coatings. In Japan, the oxime of perillaldehyde (perillartin) is used as an artificial sweetener and typically is about 2,000 times sweeter than sucrose.

Rancimat testing has shown the advantages of the *perilla* seed oil extract in accordance with a non-limiting example. This method is an accelerated oxidation test that is a simple, quick and efficient way to screen the effectiveness of the antioxidants used in liquid fats and oils. Typically, the rancimat test is an accelerated oxidation test in which the oil or fat to be tested is run at an elevated temperature exposing the sample to air accelerating the oxidation process of the oil. Auto oxidation typically occurs in a few hours instead of the months or years and the metabolites are driven off into a measuring vessel that measures the change in conductivity in one example. This would indicate the point at which the formation of volatile carboxylic acids and oxidation has occurred.

It is also possible to disperse nano- and/or micro-particles of rice or sugar cane based policosanol for providing a heart healthy dietary supplement. Such dietary supplement composition additives are disclosed in commonly assigned U.S. Pat. No. 7,959,950, the disclosure which is hereby incorporated by reference in its entirety. This human or animal dietary supplement composition includes one or more long chain (C24-C36) primary alcohols (policosanols) dispersed in food-grade oils or fats where the average policosanol particle size is greater than 2 microns and less than 10 microns in one example, and in another example, less than 100 microns.

The desired *perilla* seed oil extract is combined with various carotenoids to form an eye health composition and associated method for its use. Different carotenoids can be used, including 3,3'S-astaxanthin derived from *Haematococcus pluvialis* in combination with other carotenoids for eye health.

Reference is particularly directed to the incorporated by reference patent application Ser. Nos. 13/553,025 and 13/937,547 for general information on eye health as noted in their Background section.

With respect to humans and eye health, carotenoids have been found important with their antioxidant properties, about ten carotenoids are found in human serum. The major carotenoids in human serum are beta-carotene, alpha-carotene, cryptoxanthin, lycopene and lutein. Small amounts of zeaxanthin, phytofluene, and phytoene are found in human organs. However, of the ten carotenoids found in human serum, only two, trans- and/or meso-zeaxanthin and lutein, have been found in the human retina. Zeaxanthin is the predominant carotenoid in the central macula or foveal region and is concentrated in the cone cells in the center of the retina, i.e., the fovea. Lutein is predominantly located in the peripheral retina in the rod cells. Therefore, the eye preferentially assimilates zeaxanthin over lutein in the central macula which is a more effective singlet oxygen scavenger than lutein. It has been theorized that zeaxanthin and lutein are concentrated in the retina because of their ability to quench singlet oxygen and scavenge free radicals, and thereby limit or prevent photic damage to the retina.

Therefore only two of the about ten carotenoids present in human serum are found in the retina. Beta-carotene and lycopene, the two most abundant carotenoids in human serum, either have not been detected or have been detected only in minor amounts in the retina. Beta-carotene is relatively inaccessible to the retina because beta-carotene is unable to cross the blood-retinal brain barrier of the retinal pigmented epithelium effectively. It also is known that another carotenoid, canthaxanthin, can cross the blood-retinal brain barrier and reach the retina. Canthaxanthin, like all carotenoids, is a pigment and can discolor the skin. Canthaxanthin provides a skin color that approximates a suntan, and accordingly has been used by humans to generate an artificial suntan. However, an undesirable side effect in individuals that ingested canthaxanthin at high doses for an extended time was the formation of crystalline canthaxanthin deposits in the inner layers of the retina. Therefore, the blood-retinal brain barrier of the retinal pigmented epithelium permits only particular carotenoids to enter the retina. The carotenoids other than zeaxanthin and lutein that do enter the retina cause adverse effects, such as the formation of crystalline deposits by canthaxanthin, which may take several years to dissolve. Canthaxanthin in the retina also caused a decreased adaptation to the dark.

Investigators have unsuccessfully sought additional antioxidants to further counteract the adverse affects of singlet oxygen and free radical species on in the eye. The investigators have studied the antioxidant capabilities of several compounds, including various carotenoids. Even though the carotenoids are strong antioxidants, investigators have failed to find particular carotenoids among the 600 naturally-occurring carotenoids that effectively quench singlet oxygen and scavenge for free radical species, that are capable of crossing the blood-retinal brain barrier, that do not exhibit the adverse affects of canthaxanthin after crossing the blood-retinal brain barrier, and that ameliorate eye disease or injury and/or retard the progression of a degenerative disease of the eye and are more potent antioxidants than either lutein or zeaxanthin.

It is known that singlet oxygen and free radical species are significant contributors to central nervous system, and particularly eye injury and disease. For example, it has reported that consumption of an antioxidant, such as ascorbic acid (Vitamin C), alpha-tocopherol (Vitamin E) or beta-carotene (which is converted in vivo to lutein), can decrease the prevalence of age-related macular degeneration.

Several carotenoids, including astaxanthin, are strong antioxidants compared to beta-carotene, ascorbic acid and other widely used antioxidants in vitro. It is also known that particular carotenoids selectively cross the blood-retinal brain barrier, and that (2) certain carotenoids other than zeaxanthin and lutein that cross the blood-retinal brain barrier cause adverse affects.

Astaxanthin is a more effective antioxidant than carotenoids such as zeaxanthin, lutein, tunaxanthin, canthaxanthin, beta-carotene, and alpha-tocopherol in vitro. For example, some in vitro and in vivo studies with respect to astaxanthin demonstrated that the mean effective concentration of astaxanthin which inhibits lipid peroxidation was 500 times lower than that of alpha-tocopherol. In vitro, astaxanthin exhibits a strong quenching effect against singlet oxygen and a strong scavenging effect against free radical species. This free radical theory of retinal damage has been advanced by investigators examining the effectiveness of various antioxidants in ameliorating these diseases.

To date, investigative efforts have been directed to preventing diseases and injury because the resulting free radical-induced damage is not effectively treatable. Therefore, a need exists for a method not only to prevent or retard, but also to ameliorate, degenerative and traumatic diseases and injuries to the central nervous system, and particularly the eye. It is possible to use a therapeutically effective amount of a multi-ingredient composition that includes the *perilla* seed oil extract and mixed carotenoids comprising at least astaxanthin and desirably S,S'-astaxanthin derived from *Haematococcus pluvialis* in an example, and one or more of lutein and/or trans-zeaxanthin or meso-zeaxanthin admixed with a therapeutically effective amount of *perilla* oil in an example. The composition includes 50 to 1000 mg of *perilla* oil, and in a preferred example, 50 to 500 mg of *perilla* oil, 0.5 to 8 mg of astaxanthin, 2 to 15 mg of lutein and 0.2 to 12 mg of trans-zeaxanthin. An example of the composition includes 4 mg of astaxanthin, about 10 mg of lutein, and 1.2 mg of trans-xeazanthin. This dietary supplement composition is formulated into a single dosage capsule in an example. In another example, the 3,3'S-astaxanthin derived from *Haematococcus pluvialis* is 0.1 to 16% by weight of the *perilla* seed oil extract, the lutein is 0.4 to 30% by weight of the *perilla* seed oil extract, and the trans-zeaxanthin is 0.04 to 24% by weight of the *perilla* seed oil extract. It is possible to supplement krill oil or an algae based oil as explained below to the *perilla* seed oil extract.

The astaxanthin is preferably derived from *Haematococcus pluvialis* algae, *Pfaffia*, krill or by synthetic routes, in the free diol, monoester or diester form, for example, at a daily dose of about 0.5 to 8 mg.

It should be understood that the leading cause of visual loss among elderly persons is dry or atropic AMD, which has an increasingly important social and economic impact in the United States. As the size of the elderly population increases in this country, AMD will become a more prevalent cause of blindness than both diabetic retinopathy and glaucoma combined. Although laser treatment has been shown to reduce the risk of extensive macular scarring from the "wet" or neovascular form of the disease, there are currently no effective treatments for the vast majority of patients with wet AMD.

The Eye Diseases Prevalence Research Group (EDPRG) attributes AMD as the major cause of blindness among elderly people of European ancestry. Among white persons, AMD is believed to account for more than 50% of all blinding conditions.

The EDPRG estimates that approximately 1.2 million residents of the US are living with neovascular AMD and 970,000 are living with geographic atrophy, while 3.6 million are living with bilateral large drusen. In the next 20 years, these values are expected to increase by 50% with projected demographic shifts.

Age-related developmental changes in retinal morphology and energy metabolism, as well as cumulative effects of environmental exposures may render the neural and vascular retina and retinal pigment epithelium more susceptible to damage in late adulthood. Along with these metabolic and structural changes and exposures, the aging eye also experiences a reduction in the potency of endogenous and exogenous defense systems. Pharmacological and surgical treatment options are of limited scope and efficacy currently. They are costly and may result in complications as severe as end-stage disease. The likelihood of vision loss among persons with neovascular AMD can be reduced with anti-VEGF treatment, photodynamic therapy, and laser photocoagulation.

Nutrient-based preventative treatments for AMD development and progression have been examined in several studies including AREDSI, a NEI-sponsored study, the LAST, TOZAL and CARMIS studies for example. AREDS was a multi-center study of the natural history of AMD and cataract. AREDS included a controlled randomized clinical trial designed to evaluate the effect of pharmacological doses of zinc and/or a formulation containing nutrients with antioxidant properties (vitamin C, vitamin E, and β-carotene) on the rate of progression to advanced AMD and on visual acuity outcomes. The use of the combination of antioxidants and zinc reduced the risk of development of advanced AND in participants who had at least a moderate risk of developing AND by about 25%. The overall risk of moderate vision loss [≥15 letters on the Early Treatment Diabetic Retinopathy Study (ETDRS) chart] was reduced by 19% at 5 years.

Of approximately 600 carotenoids identified in nature in the human diet, and 20 in human serum, only two forms of dietary xanthophylls, lutein and zeaxanthin, are present in human macular pigment. Lutein represents approximately 36% of all retinal carotenoids; zeaxanthin and meso-zeaxanthin each represent about 18%.

The natural tissue distribution, biochemical, and biophysical characteristics of lutein provide a reasonable basis for speculating that this nutrient acts in biological systems as: (1) an important structural molecule within cell membranes; (2) a short-wavelength light filter; (3) a modulator of intra- and extracellular reduction-oxidation (redox) balance; and (4) a modulator in signal transduction pathways. Lutein and zeaxanthin were considered for inclusion in the AREDS formulation; however, at the time of AREDS' initiation, neither carotenoid was readily available for manufacturing in a research formulation.

The evidence base suggests that macular xanthophylls in combination with omega-3 LCPUFAs from fish oil may act as modifiable factors capable of modulating processes implicated in existing AMD pathogenesis and progression and is the basis for the on-going US Government sponsored AREDS II study. Intake of these compounds may also show merit as a well-tolerated preventive intervention. Biochemical and biophysical properties of these compounds demonstrate a capacity to modulate factors and processes that activate and are activated by exposures associated with aging. These exposures include developmental changes associated with aging, chronic light exposure, alterations in energy metabolism, and cellular signaling pathways.

Dry Eye Syndrome

According to C Stephen Foster, MD, FACS, FACR, FAAO, Clinical Professor of Ophthalmology, Harvard Medical School; Consulting Staff, Department of Ophthalmology, Massachusetts Eye and Ear Infirmary; Founder and President, Ocular Immunology and Uveitis Foundation, Massachusetts Eye Research and Surgery Institution et al' dry eye is a very common disorder affecting a significant percentage (approximately 10-30%) of the population, especially those older than 40 years.

In the United States, an estimated 3.23 million women and 1.68 million men, a total of 4.91 million people, aged 50 years and older are affected.

Dry eye is a multi-factorial disease of the tears and the ocular surface that results in symptoms of discomfort, visual disturbance, and tear film instability with potential damage to the ocular surface. Dry eye is accompanied by increased osmolarity of the tear film and inflammation of the ocular surface.

The tear layer covers the normal ocular surface. Generally, it is accepted that the tear film is made up of 3 intertwined layers, as follows:

1) A superficial thin lipid layer (0.11 μm) is produced by the meibomian glands, and its principal function is to retard tear evaporation and to assist in uniform tear spreading.

2) A middle thick aqueous layer (7 μm) is produced by the main lacrimal glands (reflex tearing), as well as the accessory lacrimal glands of Krause and Wolfring (basic tearing).

3) An innermost hydrophilic mucin layer (0.02-0.05 μm) is produced by both the conjunctiva goblet cells and the ocular surface epithelium and associates itself with the ocular surface via its loose attachments to the glycocalyx of the microplicae of the epithelium. It is the hydrophilic quality of the mucin that allows the aqueous to spread over the corneal epithelium.

The lipid layer produced by the meibomian glands acts as a surfactant, as well as an aqueous barrier (retarding evaporation of the underlying aqueous layer), and provides a smooth optical surface. It may also act as a barrier against foreign particles and may also have some antimicrobial properties. The glands are holocrine in nature, and so the secretions contain both polar lipids (aqueous-lipid interface) and nonpolar lipids (air-tear interface) as well as proteinaceous material. All of these are held together by ionic bonds, hydrogen bonds, and van der Waals forces. The secretions are subject to neuronal (parasympathetic, sympathetic, and sensory sources), hormonal (androgen and estrogen receptors), and vascular regulation. Evaporative loss is predominantly due to meibomian gland dysfunction (MGD).

The aqueous component is produced by the lacrimal glands. This component includes about 60 different proteins, electrolytes, and water. Lysozyme is the most abundant (20-40% of total protein) and also the most alkaline protein present in tears. It is a glycolytic enzyme that is capable of breaking down bacterial cell walls. Lactoferrin has antibacterial and antioxidant functions, and the epidermal growth factor (EGF) plays a role in maintaining the normal ocular surface and in promoting corneal wound healing. Albumin, transferrin, immunoglobulin A (IgA), immunoglobulin M (IgM), and immunoglobulin G (IgG) are also present.

Aqueous tear deficiency (ATD) is the most common cause of dry eye, and it is due to insufficient tear production. The secretion of the lacrimal gland is controlled by a neural reflex arc, with afferent nerves (trigeminal sensory fibers) in the cornea and the conjunctiva passing to the pons (superior salivary nucleus), from which efferent fibers pass, in the nervus *intermedius*, to the pterygopalatine ganglion and postganglionic sympathetic and parasympathetic nerves terminating in the lacrimal glands.

Keratoconjunctivitis sicca (KCS) is the name given to this ocular surface disorder. KCS is subdivided into Sjogren syndrome (SS) associated KCS and non-SS associated KCS. Patients with aqueous tear deficiency have SS if they have associated xerostomia and/or connective tissue disease. Patients with primary SS have evidence of a systemic autoimmune disease as manifested by the presence of serum auto-antibodies and very severe aqueous tear deficiency and ocular surface disease. These patients, mostly women, do not have a separate, identifiable connective tissue disease. Subsets of patients with primary SS lack evidence of systemic immune dysfunction, but they have similar clinical ocular presentation. Secondary SS is defined as KCS associated with a diagnosable connective tissue disease, most commonly rheumatoid arthritis but also SLE and systemic sclerosis.

Non-SS KCS is mostly found in postmenopausal women, in women who are pregnant, in women who are taking oral contraceptives, or in women who are on hormone replacement therapy (especially estrogen only pills). The common denominator here is a decrease in androgens, either from reduced ovarian function in the postmenopausal female or from increased levels of the sex hormone binding globulin in pregnancy and birth control pill use. Androgens are believed to be trophic for the lacrimal and meibomian glands. They also exert potent anti-inflammatory activity through the production of transforming growth factor beta (TGF-beta), suppressing lymphocytic infiltration.

Lipocalins (previously known as tear-specific prealbumin), which are present in the mucous layer, are inducible lipid-binding proteins produced by the lacrimal glands that lower the surface tension of normal tears. This provides stability to the tear film and also explains the increase in surface tension that is seen in dry eye syndromes characterized by lacrimal gland deficiency. Lipocalin deficiency can lead to the precipitation in the tear film, forming the characteristic mucous strands seen in patients with dry eye symptomatology.

The glycocalyx of the corneal epithelium contains the transmembrane mucins (glycosylated glycoproteins present in the glycocalyx) MUC1, MUC4, and MUC16. These membrane mucins interact with soluble, secreted, gel-forming mucins produced by the goblet cells (MUC5AC) and also with others like MUC2. The lacrimal gland also secretes MUC7 into the tear film.

These soluble mucins move about freely in the tear film (a process facilitated by blinking and electrostatic repulsion from the negatively charged transmembrane mucins), functioning as clean-up proteins (picking up dirt, debris, and pathogens), holding fluids because of their hydrophilic nature, and harboring defense molecules produced by the lacrimal gland. Transmembrane mucins prevent pathogen adherence (and entrance) and provide a smooth lubricating surface, allowing lid epithelia to glide over corneal epithelia with minimal friction during blinking and other eye movements. Recently, it has been suggested that the mucins are mixed throughout the aqueous layer of tears (owing to their hydrophilic nature) and, being soluble, move freely within this layer.

Mucin deficiency (caused by damage to the goblet cells or the epithelial glycocalyx), as seen in Stevens-Johnson syndrome or after a chemical burn, leads to poor wetting of the corneal surface with subsequent desiccation and epithelial damage, even in the presence of adequate aqueous tear production.

Pathophysiology

A genetic predisposition in SS associated KCS exists as evident by the high prevalence of human leukocyte antigen B8 (HLA-B8) haplotype in these patients. This condition leads to a chronic inflammatory state, with the production of auto-antibodies, including antinuclear antibody (ANA), rheumatoid factor, fodrin (a cytoskeletal protein), the muscarinic M3 receptor, or SS-specific antibodies (eg, anti-RO [SS-A], anti-LA [SS-B]), inflammatory cytokine release, and focal lymphocytic infiltration (i.e., mainly $CD4^{4+}$ T cells but also B cells) of the lacrimal and salivary gland, with glandular degeneration and induction of apoptosis in the conjunctiva and lacrimal glands. This results in dysfunction of the lacrimal gland, with reduced tear production, and loss of response to nerve stimulation and less reflex tearing. Active T lymphocytic infiltrate in the conjunctiva also has been reported in non-SS associated KCS.

Both androgen and estrogen receptors are located in the lacrimal and meibomian glands. SS is more common in postmenopausal women. At menopause, a decrease in circulating sex hormones (i.e., estrogen, androgen) occurs, possibly affecting the functional and secretory aspect of the lacrimal gland. Forty years ago, initial interest in this area centered on estrogen and/or progesterone deficiency to explain the link between KCS and menopause. However, recent research has focused on androgens, specifically testosterone, and/or metabolized androgens.

It has been shown that in meibomian gland dysfunction, a deficiency in androgens results in loss of the lipid layer, specifically triglycerides, cholesterol, monounsaturated essential fatty acids (e.g., oleic acid), and polar lipids (eg, phosphatidylethanolamine, sphingomyelin). The loss of polar lipids (present at the aqueous-tear interface) exacerbates the evaporative tear loss, and the decrease in unsaturated fatty acids raises the melting point of meibum, leading to thicker, more viscous secretions that obstruct ductules and cause stagnation of secretions. Patients on anti-androgenic therapy for prostate disease also have increased viscosity of meibum, decreased tear break-up time, and increased tear film debris, all indicative of a deficient or abnormal tear film.

It is known that in various tissues pro-inflammatory cytokines may cause cellular destruction. For example including interleukin 1 (IL-1), interleukin 6 (IL-6), interleukin 8 (IL-8), TGF-beta, TNF-alpha, and RANTES, are altered in patients with KCS. IL-1 beta and TNF-alpha, which are present in the tears of patients with KCS, cause the release of opioids that bind to opioid receptors on neural membranes and inhibit neurotransmitter release through NF-K β production. IL-2 also binds to the delta opioid receptor and inhibits cAMP production and neuronal function. This loss of neuronal function diminishes normal neuronal tone, leading to sensory isolation of the lacrimal gland and eventual atrophy.

Pro-inflammatory neurotransmitters, such as substance P and calcitonin gene related peptide (CGRP), are released, which recruit and activate local lymphocytes. Substance P also acts via the NF-AT and NF-K β signaling pathway leading to ICAM-1 and VCAM-1 expression, adhesions molecules that promote lymphocyte homing and chemotaxis to sites of inflammation. Cyclosporin A is an NK-1 and NK-2 receptor inhibitor that can down-regulate these signaling molecules and is a novel addition to the therapeutic armamentarium for dry eye, being used to treat both aqueous tear deficiency and meibomian gland dysfunction. It has been shown to improve the goblet cell counts and to reduce the numbers of inflammatory cells and cytokines in the conjunctiva.

These pro-inflammatory cytokines, in addition to inhibiting neural function, may also convert androgens into estrogens, resulting in meibomian gland dysfunction, as discussed above. An increased rate of apoptosis is also seen in conjunctival and lacrimal acinar cells, perhaps due to the cytokine cascade. Elevated levels of tissue-degrading enzymes called matrix metalloproteinases (MMPs) are also present in the epithelial cells.

Mucin synthesizing genes, designated MUC1-MUC17, representing both transmembrane and goblet-cell secreted, soluble mucins, have been isolated, and their role in hydration and stability of the tear film are being investigated in patients with dry eye syndrome. Particularly significant is MUC5AC, expressed by stratified squamous cells of the conjunctiva and whose product is the predominant component of the mucous layer of tears. A defect in this and other mucin genes may be a factor in dry eye syndrome development. In addition to dry eye, other conditions, such as ocular cicatricial pemphigoid, Stevens-Johnson syndrome, and vitamin A deficiency, which lead to drying or keratinization of the ocular epithelium, eventually lead to goblet cell loss. Both classes of mucins are decreased in these diseases, and, on a molecular level, mucin gene expression, translation, and posttranslational processing are altered.

Normal production of tear proteins, such as lysozyme, lactoferrin, lipocalin, and phospholipase A2, is decreased in KCS.

It is clear from the above discussion that common causes of dry eye syndromes may be ameliorated by treatment with anti-inflammatory agents such as topical corticosteroids, topical cyclosporine A and/or topical/systemic omega-3 fatty acids.

Studies that examined the association of dietary lutein/zeaxanthin intake with advanced AMD have yielded inverse relationships that are statistically significant. The magnitude of odds ratios in these studies ranged from 0.1 to 0.7. Both sets of findings are germane in guiding applied clinical research on prevention and treatment of retinal disease, since: (1) tissue concentrations of DHA, lutein, and zeaxanthin per unit area are substantially higher in the retina than elsewhere in the body; and (2) retinal tissue status of these compounds is modifiable and dependent upon intake.

The AREDS II study protocol (concluded its scientific rational by stating: "There is a compelling need to implement a clinical trial on nutrients that are both concentrated in the retina and implicated in modulation of pathogenic factors and processes of AMD."

It has been well established that lutein and trans-zeaxanthin are present in human retinal tissue and that they function to protect the eye from photo induced injury. The CARMIS study, which included a mixture of lutein, trans-zeaxanthin and astaxanthin, is the only clinical trial which reported the use of astaxanthin. Unfortunately, there have been no reports of the use of astaxanthin alone in any human clinical trial for the prevention or amelioration of dry AMD. The CARMIS study failed to determine if supplementation with astaxanthin alone is a key determinate of the positive outcomes of the study or that astaxanthin deposited on retinal epithelial cells. One possible interpretation of the CARMIS study is that lutein and zeaxanthin alone provided the observed benefits of the formulation employed, or in another interpretation that astaxanthin in combination with lutein and zeaxanthin provided the observed benefits. However, in no possible interpretation can one conclude unequivocally that astaxanthin alone prevents or ameliorates dry AMD.

In addition, the work of Tso as in U.S. Pat. No. 5,527,533, the disclosure which is hereby incorporated by reference in its entirety, and as disclosed in the article entitled, "Experiments on Visual Cells by Nature and Man: In Search of Treatment for Photoreceptor Degeneration," Investigative Opthalmology and Visual Science, 30(12), pages 2421-2454 (December 1989), though claiming utility of astaxanthin for prevention or amelioration of dry AMD in humans, was not based on clinical trials performed on human subjects but instead on a different mammalian species, namely in rats.

Therefore, there remains no conclusive evidence that astaxanthin alone can prevent or ameliorate dry AMD in man since no human study has ever been performed using astaxanthin supplementation alone, nor has any human study shown that astaxanthin actually deposits anywhere in the human retina, the first required step to retinal protection by this powerful carotenoid.

Potential Roles of Polyunsaturated Fatty Acids in Eye Physiology

An inverse relationship of dietary omega-3 LCPUFA intake with advanced AMD has been reported in six studies examining the issue. For prevalent disease, the magnitude of odds ratios for highest versus lowest omega-3 LCPUFA intake ranged from 0.4 to 0.9.

Among these studies, the one containing the largest number of subjects with neovascular or "wet" AMD yielded a significantly lower likelihood of having the disease among participants reporting the highest consumption of omega-3.

The scientific literature is replete with the certain human benefits of triacylglyceride bound EPA and DHA found in fish oil and fish oil concentrates and more recently the potential utility of phospholipid bound EPA and DHA found in krill oil derived from *Euphasia superba* or Antarctic krill.

The cardiovascular benefits as well as the anti-inflammatory benefits of such fish and krill oils, and in particular triacylglyceride bound EPA and DHA derived from fish oils as well as algae derived triacylglyceride bound DHA are well known. Such algae derived DHA is used in large part as a supplement in infant formulas to ensure brain health in the developing fetus and in infants. Seed oils are also a potent source as explained above.

LCPUFAs affect factors and processes implicated in the pathogenesis of vascular and neural retinal disease. Evidence characterizing structural and functional properties of LCPUFAs indicates that these nutrients may operate both as: (1) essential factors in the visual-sensory process, and (2) protective agents against retinal disease.

Docosahexaenoic Acid (DHA) is the major structural lipid of retinal photoreceptor outer segment membranes. Tissue DHA status affects retinal cell signaling mechanisms involved in phototransduction. Tissue DHA insufficiency is associated with conditions characterized by alterations in retinal function, and functional deficits have been ameliorated with DHA supplementation in some cases. Biophysical and biochemical properties of DHA may affect photoreceptor function by altering membrane permeability, fluidity, thickness, and lipid phase properties. DHA may operate in signaling cascades to enhance activation of membrane-bound retinal proteins. DHA may also be involved in rhodopsin regeneration.

DHA and Eicosapentaenoic Acid (EPA) may serve as protective agents because of their effect on gene expression, retinal cell differentiation, and survival. DHA activates a number of nuclear hormone receptors that operate as transcription factors for molecules that modulate redox-sensitive and proinflammatory genes; these include the peroxisome proliferator-activated receptor-α (PPAR-α) and the retinoid X receptor (RXR). In the case of PPAR-α, this action is thought to prevent endothelial cell dysfunction and vascular remodeling through inhibition of vascular smooth muscle cell proliferation, inducible nitric oxide synthase production, interleukin(IL)-1 induced cyclooxygenase (COX)-2 production, and thrombin-induced endothelin-1 production.

Research on model systems demonstrates that omega-3 LCPUFAs also have the capacity to affect production and activation of angiogenic growth factors, arachidonic acid-based proangiogenic eicosanoids, and matrix metalloproteinases involved in vascular remodeling.

EPA depresses vascular endothelial growth factor (VEGF)-specific tyrosine kinase receptor activation and expression. VEGF plays an essential role in induction of endothelial cell migration and proliferation, microvascular permeability, endothelial cell release of metalloproteinases and interstitial collagenases, and endothelial cell tube formation. The mechanism of VEGF receptor down-regulation is believed to occur at the tyrosine kinase nuclear factor-kappa B (NFkB) site because EPA treatment causes suppression of NFkB activation. NFkB is a nuclear transcription factor that up-regulates COX-2 expression, intracellular adhesion molecule (ICAM), thrombin, and nitric oxide synthase. All four factors are associated with vascular instability. COX-2 drives conversion of arachidonic acid to a number of angiogenic and pro-inflammatory eicosanoids.

Although the mechanistic benefits of dietary supplementation with EPA and DHA polyunstaruated fatty acids in triacylglyceride form are well know, it remains speculative that such triacylglyceride bound EPA and DHA can improve vision. Such hypothesis is now under exploration under the National Eye Institute's 5-year AREDS II study.

Cataracts

A cataract is an opacity, or clouding, of the lens of the eye. The prevalence of cataracts increases dramatically with age. It typically occurs in the following way. The lens is an elliptical structure that sits behind the pupil and is normally transparent. The function of the lens is to focus light rays into images on the retina (the light-sensitive tissue at the back of the eye).

In young people, the lens is elastic and changes shape easily, allowing the eyes to focus clearly on both near and distant objects. As people reach their mid-40s, biochemical changes occur in the proteins within the lens, causing them to harden and lose elasticity. This causes a number of vision problems. For example, loss of elasticity causes presbyopia, or far-sightedness, requiring reading glasses in almost everyone as they age.

In some people, the proteins in the lens, notably those called alpha crystallins, may also clump together, forming cloudy (opaque) areas called cataracts. They usually develop slowly over several years and are related to aging. In some cases, depending on the cause of the cataracts, loss of vision progresses rapidly. Depending on how dense they are and where they are located, cataracts can block the passage of light through the lens and interfere with the formation of images on the retina, causing vision to become cloudy.

Nuclear cataracts form in the nucleus (the inner core) of the lens. This is the most common variety of cataract associated with the aging process. Cortical cataracts form in the cortex (the outer section of the lens). Posterior subcapsular cataracts form toward the back of a cellophane-like capsule that surrounds the lens. They are more frequent in people with diabetes, who are overweight, or those taking steroids. Although the causes of cataract formation remain largely unknown, researchers have been focusing on particles called oxygen-free radicals as a major factor in the development of cataracts. They cause harm in the following way:

Oxygen-free radicals (also called oxidants) are molecules produced by natural chemical processes in the body. Toxins, smoking, ultraviolet radiation, infections, and many other factors can create reactions that produce excessive amounts of these oxygen-free radicals. When oxidants are overproduced, these chemical reactions can be very harmful to nearly any type of cell in the body. At times these reactions can even affect genetic material in cells.

Cataract formation is one of many destructive changes that can occur with overproduction of oxidants, possibly in concert with deficiencies of an important protective antioxidant called glutathione. Glutathione occurs in high levels in the eye and helps clean up these free radicals. One theory is that in the aging eye, barriers develop that prevent glutathione and other protective antioxidants from reaching the nucleus in the lens, thus making it vulnerable to oxidation. Sunlight consists of ultraviolet (referred to as UVA or UVB) radiation, which penetrates the layers of the skin. Both UVA and UVB have destructive properties that can promote cataracts. The eyes are protected from the sun by eyelids and the structure of the face (overhanging brows, prominent cheekbones, and the nose). Long-term exposure to sunlight, however, can overcome these defenses.

UVB radiation produces the shorter wavelength, and primarily affects the outer skin layers. It is the primary cause of sunburn. It is also the UV radiation primarily responsible for cataracts. Long-term exposure to even low levels of UVB radiation can eventually cause changes in the lens, including pigment changes, which contribute to cataract development. (UVB also appears to play a role in macular degeneration, an age-related disorder of the retina.) UVA radiation is composed of longer wavelengths. They penetrate more deeply and efficiently into the inner skin layers and are responsible for tanning. The main damaging effect of UVA appears to be the promotion of the release of oxidants. Cataracts are common side effects of total body radiation treatments, which are administered for certain cancers. This observation indicates that ionizing radiation, which produces large numbers of free radicals dramatically accelerates cataract formation.

Glaucoma and its treatments, including certain drugs (notably miotics) and filtering surgery, pose a high risk for cataracts. The glaucoma drugs posing a particular risk for cataracts including demecarium (Humorsol), isoflurophate (Floropryl), and echothiophate (Phospholine). Uveitis is chronic inflammation in the eye, which is often caused by an autoimmune disease or response. Often the cause is unknown. It is a rare condition that carries a high risk for cataracts. It is not clear whether nutrition plays a significant role in cataract development. Dark colored (green, red, purple, and yellow) fruits and vegetables usually have high levels of important plant chemicals (phytochemicals) and may be associated with a lower risk for cataracts.

In analyzing nutrients, researchers have focused on antioxidants and carotenids. Studies have not demonstrated that antioxidant vitamin supplements (such as vitamins C and 5) help prevent cataracts. Lutein and zeaxanthin are the two carotenids that have been most studied for cataract prevention. They are xanthophylls compounds, which are a particular type of carotenid. Lutein and zeaxanthin are found in the lenses of the eyes. Some evidence indicates that xanthophyll-rich foods (such as dark green leafy vegetables) may help retard the aging process in the eye and protect against cataracts. However, there is not enough evidence to suggest that taking supplements with these carotenoids lowers the risk of cataract formation. Since little is known about the exact mechanism for formation of cataracts, it is not surprising that there are no known drugs or dietary supplements including the carotenoids that prevent cataract formation there remains a need to find a suitable preventative treatment to prevent or ameliorate further cataract formation. Since no drugs can reverse nor prevent cataract formation, the only current treatment suitable for advanced cataract in humans is lens replacement surgery.

The ability of a carotenoid to pass the blood-retinal brain barrier is important because carotenoids are not synthesized by the human body. The only source of carotenoids for humans is dietary intake. Furthermore, humans have a very limited ability to modify carotenoids. Therefore, the carotenoids accumulate in various organs in the ingested form. Accordingly, if a particular carotenoid is unable to cross the blood-retinal brain barrier, the carotenoid cannot accumulate in the retina and serve as an antioxidant.

Furthermore, some carotenoids that are not normal constituents of human plasma, but have the ability to cross the blood-retinal brain barrier, have demonstrated adverse effects on the retina. Canthaxanthin which is intentionally ingested to provide an artificial suntan has accumulated in the retina in the form of crystals and has temporarily affected eye adaptation to the dark. In addition, beta-carotene has a very limited ability to cross the blood-retinal brain barrier.

Therefore, even though the carotenoids are known as strong antioxidants and are present in abundant supply, the carotenoids have not been used for the treatment of central nervous system damage, or eye damage, caused by disease or injury. The carotenoids investigated to date either could not effectively cross the blood-retinal barrier (i.e., beta-carotene) or adversely affected the eye (i.e., canthaxanthin).

In accordance with a non-limiting example, the composition comprises a therapeutically effective amount of a multi-ingredient composition of mixed carotenoids including at least S,S'-astaxanthin derived from *Haematococcus pluvialis*, and one or more of lutein and/or trans-zeaxanthin or meso-zeaxanthin admixed with a therapeutically effective amount of *perilla* seed oil extract. In an example, the composition includes 50 to 500 mg of *perilla* oil, 0.5 to 8 mg of astaxanthin, 2 to 15 mg of lutein and 0.2 to 12 mg of trans-zeaxanthin. The composition contains naturally-occurring compounds and is a potent antioxidant and anti-inflammatory composition, which can be is used in a method to ameliorate and retard, or prevent, cell damage in an individual suffering from a degenerative, inflammatory disease or injury to the eye. In accordance with another non-limiting example, the administration of a therapeutically-effective amount of the composition to an individual prevents, retards and/or ameliorates free radical-induced damage resulting from eye disease or injury. For example, damage to a retina can result from either photic injury, neurodegenerative disease or an ischemic insult followed by reperfusion. With respect to damage from photic injury, the composition decreases the loss of photoreceptor cells. With respect to damage from ischemic insult, the composition ameliorates the loss of ganglion cells and the inner layers of the retinal neuronal network.

None of the carotenes tested to date, and most of the xanthophylls tested to date do not pass through the blood brain barrier with a few notable exceptions. These exceptions include lutein, trans-zeaxanthin, canthaxanthin and astaxanthin.

Human serum typically contains about ten carotenoids. The major carotenoids in human serum include beta-carotene, alpha-carotene, cryptoxanthin, lycopene and lutein. Small amounts of zeaxanthin, phytofluene and phytoene are also found in human organs. However, of all of these carotenoids, only zeaxanthin and lutein are found in the human retina. In addition to certain carotenoids, the retina also has the highest concentration of polyunsaturated fatty acids of any tissue in the human body. These polyunsaturated fatty acids are highly susceptible to free radial and singlet oxygen induced decomposition. Therefore there is an absolute need to protect these polyunsaturated fatty acids, which make up a portion of the cellular membrane bi-layer, from photo induced free radical or singlet oxygen degradation.

It has been theorized that zeaxanthin and lutein are concentrated in the retina because of their ability to quench singlet oxygen and to scavenge free radicals, because they pass the blood and eye brain barriers and are required in the oxygen rich environment of the retina to prevent light mediated free radical damage to the retina.

In fact, zeaxanthin is the predominant carotenoid found in the central portion of the retina and more specifically is located in concentration in the retinal cones located in the central area of the retina (i.e., the macula). Lutein, on the other hand, is located in the peripheral area of the retina in the rod cells. Therefore, the eye preferentially accumulates zeaxanthin over lutein in the critical central macular retinal area, (zeaxanthin interestingly, is a much more effective singlet oxygen scavenger than lutein), where the greatest level of light impinges.

Biochemists have determined the exact, yet complicated, mechanism for light sensory response in the eye. It involves a key protein called rhodopsin whose structure includes a bound polyunsaturated compound called retinal (retinal is structurally related to vitamin A). When light enters the eye, cis-retinal isomerizes to all its all-trans isomer, causing disassociation of itself from its protein carrier. The disassociation triggers a complicated cascade leading to nerve based transmission of electrons to the brain via the optic nerve. All of this "photochemistry" takes a mere 200 femtoseconds to occur making it one of the fastest biochemical to electron transformations known.

Chemists have learned that the retina is highly susceptible to polymerization by localized free radicals and highly reactive singlet oxygen. Because the retina is a strong absorber of light and because the retina is highly vascularized and thus rich in dissolved oxygen, nature has provided zeaxanthin as the key retinal carotenoid for protection of the central foveal region of the retina from light induced damage at that point in the center of the retina where the most significant light impingement occurs.

Clinical studies in man indicate that photic injury is a cause of age related macular degeneration because of the cumulative effect of repeated photic insult leading to the gradual loss of photoreceptor cells.

There have been many clinical trials designed to support the supplementation of the diet with lutein, however, as of 2007, there appears to be no unequivocal evidence that lutein supplementation is necessary in eye healthcare despite its wide acceptance as a supplement. This may simply imply that supplementation with extra lutein is not necessary since it is a readily available xanthophyll in many vegetables. More recently trans-zeaxanthin and meso-zeaxanthin have also entered the marketplace as an eye healthcare supplements which indeed makes sense. However, is there yet a better carotenoid meeting all the requirements associated with eye/blood/brain barrier transport, accumulation in the macula and capable of long term use? The answer is found in the xanthophyll astaxanthin.

Dr. Mark Tso, at the Univ. of Ill, has demonstrated that astaxanthin is one such naturally occurring antioxidant meeting all of these critical criteria in rats. Astaxanthin is the carotenoid xanthophyll responsible for the red color in salmon, lobster, krill, crab, other shell fish and in the micro algae Haematoccous pluvialis. The latter source has made astaxanthin readily available worldwide for such uses. U.S. Pat. No. 5,527,533 was issued to the Univ. of Ill. describing the use of astaxanthin more fully in eye related diseases and which is hereby incorporated by in its entirety.

In addition, astaxanthin is a much more powerful antioxidant than canthoaxanthin, beta-carotene, zeaxanthin, lutein and alpha-tocopherol. Some researchers have discovered that astaxanthin is 550 times more potent than alpha-tocopherol, 27.5 times more potent than lutein and 11 times more potent that beta-carotene in quenching singlet oxygen. In addition, other researchers discovered that natural astaxanthin is 14 times more potent than alpha-tocopherol, 54 times more potent that beta-carotene and 65 times more potent that ascorbic acid (Vitamin C) in scavenging oxygen free radicals. Thus, though there are dramatic differences in the potency of astaxanthin when comparing the quenching of singlet oxygen and the scavenging of oxygen free radicals, it is clear that astaxanthin compares very favorably to zeaxanthin and lutein, the two carotenoids that are found naturally in the retina.

There is one more aspect of carotenoids, namely that some carotenoids can act as pro-oxidants. This is important since a carotenoid with pro-oxidant capability actually causes oxidation to occur in the body when high concentrations are present in tissue. Another researcher showed that beta-carotene, lycopene and zeaxanthin can become pro-oxidants under certain conditions. Since humans already have an abundant source of lutein and trans-zeaxanthin in their diets from many vegetable sources and are already present in the human eye, it appears that astaxanthin with its unique qualifying properties, unlike lutein or trans-zeaxanthin, may be the eye healthcare supplement of choice. With astaxanthin's extraordinarily potent antioxidant properties, its ability to cross the blood brain/eye barrier and concentrate in the retinal macula in other mammalian species, without the side effects seen with canthaxanthin, and in light of Tso's contributions, astaxanthin, in a convenient dietary supplement presentation, may emerge as the pre-eminent new ingredient addition to lutein and/or zeaxanthin eye healthcare supplementation for the management of eye related oxidative stress and thus the prevention and mitigation of degenerative diseases of the eye such as age related macular degeneration (ARMD) and cataract formation if astaxanthin deposition can be experimentally confirmed in human retinal tissue.

In addition, Tso found that light induced damage, photoreceptor cell damage, ganglion cell damage and damage to neurons of the inner retinal layers can be prevented or ameliorated by the use of astaxanthin including neuronal damage from ischemic, photic, inflammatory and degenerative insult in rats. Tso discloses the use of astaxanthin across a wide range of eye diseases including age related macular degeneration, diabetic neuropathy, cystoid macular edema, central retinal arterial and veneous occlusion, glaucoma and inflammatory eye diseases such as retinitis, uveitis, iritis, keratitis and scleritis, all disease states common to eye insult by oxidative species such as free radicals however this work was never confirmed in humans.

Oral administration of astaxanthin confirms that it is at least transported into human blood stream, however, its deposition in human retinal tissue has never been confirmed.

Astaxanthin is the major pigment of certain micro algae and crustaceans. Astaxanthin is a lipid-soluble pigment primarily used for pigmenting cultured fish, like salmon, which must ingest astaxanthin to yield consumer-acceptable pink-colored salmon muscle. Astaxanthin also is an antioxidant which is about 100 to about 1000 times more effective than alpha-tocopherol.

The prime source of commercial S,S'-astaxanthin is micro algae, and, to a very small extent, is found in krill oil derived from *Euphasia superba* (Antarctic Krill). Astaxanthin also is available synthetically, however synthetic astaxanthin may not be safe for use in humans since it contains 3 known enantiomers including R,R', R, S' and S,S' which are not easily nor economically separated two of which have unknown human safety data. The preferred naturally-occurring S,S'-astaxanthin can be used in the composition and method of the present invention.

As previously noted, the retinal pigment epithelium protects the retina by providing a blood-retinal brain barrier. The barrier excludes plasma constituents that are potentially harmful to the retina. As also previously noted, the blood-retinal brain barrier permits lutein and zeaxanthin to enter the retina, and excludes other carotenoids present in human serum, including beta-carotene which is the most abundant carotenoid in human serum. Astaxanthin is not a naturally-occurring constituent in the retina. Therefore, the presence of a physiologically significant amount of astaxanthin in the retina of rats may illustrate the ability of astaxanthin to readily cross the blood-retinal brain barrier into the retina of humans. The optimal dose of the composition can be determined by a person skilled in the art after considering factors such as the disease or injury to be treated, the severity of the central nervous system damage by oral administration. The daily dose of composition can be administered daily or in accordance with a regimen determined by a person skilled in the art, with the length of treatment depending upon the severity and nature of the injury to the central nervous system, the need to improve accommodation or to control dry eye syndrome.

The composition can be administered to an individual orally such as in a single dose capsule. When administered orally, the composition, for example, can be in the form of a liquid preparation. The administration of the composition to an individual suffering from an eye injury or disease, such as free radical-induced injury, benefits the vision of the individual by preventing further photoreceptor cells from damage or destruction. The free radical-induced damage can be attributed to light-induced injury or to injury resulting from an ischemic insult and subsequent reperfusion or neurodegenerative diseases. The administration of astaxanthin also helps prevent and retard photic injury in addition to ameliorating photic injury.

The administration of the composition ameliorates photoreceptor cell damage that is light induced, and ameliorates ganglion cell damage that is induced by ischemic insult and subsequent reperfusion. The administration of astaxanthin also retards the progress of degenerative eye diseases and benefits the vision of individuals suffering from a degenerative eye disease, such as age-related macular degeneration.

The administration of the composition also provides a method of treating ischemic retinal diseases, such as diabetic retinopathy, cystoid macular edema, central retinal arterial occlusion, central retinal venous occlusion and glaucoma. In addition, the composition is useful in treating inflammatory diseases of the eye such as retinitis, uveitis, iritis, keratitis and scleritis wherein free radicals are produced in abundance, the prevention of cataracts and the treatment of certain causes of dry eye syndromes.

Therefore, the antioxidant properties of the composition, coupled with the ability of the composition to cross the blood-retinal brain barrier, admixed with anti-inflammatory sources of EPA and DHA and the lack of toxicity of the composition and the lack of adverse side effects associated with the composition, make the composition a useful composition to prevent or ameliorate such eye related diseases, dry eye syndrome and/or cataracts and dry eye syndromes.

The carotenoids admixed with the *perilla* seed oil extract in this example should be able to address not only the eye diseases known to be ameliorated by carotenoids but also the inflammatory diseases of the eye (including but not limited to dry eye syndrome) associated with the known anti-inflammatory activity of omega-3's.

Astaxanthin is also known to reduce C-Reactive Protein (C-RP) blood levels in vivo. For example, in human subjects with high risk levels of C-RP three months of astaxanthin treatment resulted in 43% drop in the patient population's serum C-RP levels a drop which is below the unacceptable cardiovascular event risk level. Astaxanthin is so powerful that it has been shown to negate the pro-oxidant activity of Vioxx in vitro, a COX-2 inhibitor belonging to the NSAIDS drug class which is known to cause cellular membrane lipid per-oxidation leading to heart attacks and strokes. For this reason Vioxx was subsequently removed from the US market by the FDA. Astaxanthin is also absorbed in vitro by lens epithelial cells where it suppresses UVB induced lipid per-oxidative mediated cell damage at umol/L concentrations. Reduction of C-Reactive protein (CRP), reduction of LDL oxidation and an increase in the omega-3 index in vivo would presumably all be important positive contributors to cardiovascular health since each are well know biomarkers for cardiovascular health risk.

Astaxanthin has an excellent safety record. A conducted study obtained the results as follows:

Oral LD 50: 600 mg/kg (rats);
NOAEL: 465 mg/kg (rats); or
Serum Pharmacokinetics: Stewart et al. 2008
1) $T_{1/2}$: 16 hours;
2) $T_{max}$: 8 hours;
3) $C_{max}$: 65 µg/L.

At eight weeks of supplementation at 6 mg per day, there was no negative effect in healthy adults. Astaxanthin has three prime sources, e.g., 3 mg astaxanthin per 240 g serving of non-farmed raised salmon or a 1% to 12% astaxanthin oleoresin or 1.5-2.5% beadlet derived from microalgae. Literature references pertinent to the above discussion can be found in Lee et al., Molecules and Cells 16(1): 97-105, 2003; Ohgami et al., Investigative Ophthalmology and Visual Science 44(6): 2694-2701, 2003; Spiller et al., J. of the American College of Nutrition 21(5): October 2002; and Fry et al., University of Memphis, Human Performance Laboratories, 2001 and 2004, Reports 1 and 2.

It should be understood that different proportions of ingredients and percentages in compositions and in the reaction product can be used depending on end use applications and other environmental and physiological factors when treating a patient condition.

The astaxanthin may be derived from *Haematococcus pluvialis* algae, *Pfaffia*, krill, or by synthetic routes, in the known free dial, monoester or diester form, and in one example, at a daily dose of 0.5-8 mg. The composition may also include an n-3 (omega-3) fatty acid rich oil derived from fish oil, algae oil, flax seed oil, or chia seed oil when the n-3 fatty acid comprises alpha-linolenic, stearidonic, eicosapentaenoic or docosapentaenoic acid. The composition may include naturally-derived and synthetic antioxidants that are added to retard degradation of fatty acids and astaxanthin.

Although a *perilla* seed oil extract is disclosed in combination with the carotenoids, including astaxanthin, it should be understood that other oils may be used either singularly or in combination with the *perilla* seed oil extract and with the carotenoids as disclosed, for example, different marine oils including a fish oil and/or krill oil and a fish oil derived choline phospholipid bound EPA and DHA. The different oils may include a shrimp mince and/or shell derived oils. There could also be an algae based oil added.

The oils from *perilla* seed oil extract may be substituted or supplemented with krill oil. The composition may include EPA and DHA functionalized as marine phospholipids and acyltriglycerides derived from krill. Some of these components are explained in the following chart:

| Components PHOSPHOLIPIDS | Percentage (%) |
|---|---|
| PC, PE, PI, PS, SM, CL | >40 |
| OMEGA-3 (functionalized on PL) | >30 |
| Eicosapentaenoid Acid (EPA)* | >17 (15% in one example and 10% in another) |
| Docosahexaenoid Acid (DHA)+ | >11 (9% in one example and 5% in another) |

Krill oil may be substituted or supplemented with the *perilla* seed oil extract and carotenoid composition and is typically produced from Antarctic krill (euphausia superba), which is a zooplankton (base of food chain). It is one of the most abundant marine biomass of about 500 million tons according to some estimates. Antarctic krill breeds in the pure uncontaminated deep sea waters. It is a non-exploited marine biomass and the catch per year is less than or equal to about 0.02% according to some estimates.

The krill oil in one example is derived from *Euphasia* spp., comprising Eicosapentaenoic (EPA) and Docosahexaenoic (DHA) fatty acids in the form of triacylglycerides and phospholipids, although not less than 1% EPA and 5% DHA has been found advantageous. In another example, the krill oil includes at least 15% EPA and 9% DHA, of which not less than 45% are in the form of phospholipids, and in one example, greater than 50%. The composition can be delivered advantageously for therapeutic results with 1-4000 mg of krill oil delivered per daily dose.

The *perilla* seed oil may also include an n-3 (omega-3) fatty acid rich oil derived from fish oil, algae oil, flax seed oil, or chia seed oil when the n-3 fatty acid comprises alpha-linolenic, stearidonic, eicosapentaenoic or docosapentaenoic acid. The composition may include naturally-derived and synthetic antioxidants that are added to retard degradation of fatty acids.

Details of a type of CO2 extraction and processing technology (as supercritical CO2 extraction) and peroxidation blocker technology that can be used are disclosed in commonly assigned U.S. Pat. Nos. 8,652,544 and 8,586,104, the disclosures which are hereby incorporated by reference in their entirety.

It is possible to use as a supplemental oil a fish oil derived, choline based, phospholipid bound omega-3 fatty acid mixture including phospholipid bound polyunsaturated EPA and DHA to improve blood lipid profiles and reduce LDL either alone or admixed with other ingredients, for example, an LDL per-oxidation blocker. One commercially available example of a mixture of fish oil derived, choline based, phospholipid bound fatty acid mixture including polyunsaturated EPA and DHA is a phospholipid, omega-3 preparation, which is derived from natural fish oil. One example of such composition is described below:

| Ingredients (g/100 g): | |
|---|---|
| Pure Marine Phospholipids | n.l.t. 15 |
| DHA* | n.l.t. 12 |
| EPA** | n.l.t. 7 |
| Omega-3 | n.l.t. 22 |
| Omega-6 | <3 |
| Analytical Data: | |
| Peroxide value (meq/Kg) | n.m.t. 5 |
| Loss on Drying (g/100 g) | n.m.t. 2 |
| Physical Properties: | |
| Consistency | Viscous Liquid |

*Docosahexaenoic acid
**Eicosapenteanoic acid

The composition may also be supplemented with an n-3 (omega-3) fatty acid rich oil derived from fish oil, algae oil, flax seed oil, or chia seed oil wherein the n-3 fatty acid source comprises alpha-linolenic, stearidonic, eicosapentaenoic or docosapentaenoic acid. The composition may include naturally-derived and synthetic antioxidants that are added to retard degradation of fatty acids such as tocopherols, tocotrienols, carnosic acid or Carnosol and/or astaxanthin.

It is known that algae can be an important source for omega-3 fatty acids such as EPA and DHA and can be used with the carotenoids. It is known that fish and krill do not produce omega-3 fatty acids but accumulate those fatty acids from the algae they consume. Omega-3 bioavailability varies and is made available at the site of physiological activity depending on what form it is contained. For example, fish oil contains omega-3 fatty acids in a triglyceride form that are insoluble in water and require emulsification by bile salts via the formation of micelles and subsequent digestion by enzymes and subsequent absorption. Those omega-3 fatty acids that are bound to polar lipids, such as phospholipids and glycolipids, however, are not dependent on bile for digestion and go through a simpler digestion process before absorption. Thus, these omega-3 fatty acids, such as from an algae based oil, have greater bioavailability for cell growth and functioning as compared to the omega-3 triglycerides of fish oil and can be used with the carotenoids in some examples. There are many varieties of algae that contain EPA conjugated with phospholipid and glycolipid polar lipids or contain EPA and DHA conjugated with phospholipids and glycolipids.

Throughout this description, the term "algae" or "microalgae" may be used interchangeably to each other with microalgae referring to photosynthetic organisms that are native to aquatic or marine habitats and are too small to be seen easily as individual organisms with the naked eye. When the term "photoautotropic" is used, it refers to growth with light as the primary source of energy and carbon dioxide as the primary source of carbon. Other forms of biomass that may encompass algae or microalgae may be used and the term "biomass" may refer to a living or recently dead biological cellular material derived from plants or animals. The term "polar" may refer to the compound that has portions of negative and/or positive charges forming negative and/or positive poles. The term "oil" may refer to a combination of fractionable lipid fractions of a biomass. As known to those skilled in the art, this may include the entire range of various hydrocarbon soluble in non-polar solvents and insoluble, or relatively insoluble in water as known to those skilled in the art. The microalgae may also include any naturally occurring species or any genetically engineered microalgae to have improved lipid production.

Algae based oil may be substituted for krill oil in an example and supplemented to the *perilla* seed oil extract. This algae based oil may provide an algae sourced EPA or an EPA/DHA based oil in which oils are present in phospholipid and glycerolipid forms, as glycolipids. Different algae based oils derived from different microalgae may be used. One preferred example algae based oil has the EPA titre higher than the DHA as compared to a class of omega-3's from fish oils that are triacylglycerides. These algae based oils are rich in EPA and in the phospholipid and glycolipid forms. An example marine based algae oil is produced by Parry Nutraceuticals as a division of EIB Parry (India) Ltd. as an omega-3 (EPA) oil.

The following first table shows the specification of an algae based oil as manufactured by Parry Nutraceuticals identified above, followed by a second table for a fatty acid profile chart of that algae based oil. A third table is a comparative chart of the fatty acid profiles for non-algae based oils. These charts show that the algae based oil has a high EPA content of phospholipids and glycolipids. The algae based oils may be processed to enrich selected constituents using supercritical $CO_2$ and/or solvent extractions as noted above and other techniques.

| SPECIFICATION: ALGAE BASED OIL | | | |
|---|---|---|---|
| PARAMETERS | SPECIFICATION | SOP. NO | TEST METHOD/ REFERENCE |
| Physical Properties | | | |
| Appearance | Viscous oil | QA - 88 | In house |
| Color | Brownish black | QA - 88 | In house |
| Odor | Characteristic | QA - 88 | In house |
| Taste | Characteristic | QA - 88 | In house |
| General Composition | | | |
| Loss on drying (%) | 2.0-3.0 | QA - 038 | USP <731> Loss on drying |
| Ash (%) | 0.5-1.0 | QA - 080 | AOAC Official Method 942.05, 16th Edition |
| Protein (%) | 1.0-2.0 | QA - 021 | AOAC Official method 978.04, 16th Edn. |
| Carbohydrate (%) | 1.0-2.0 | | AOAC 18th Edn 2006/By Difference |
| Residual Solvent (ppm) | NMT 100 | QA - 074 | GC - Head Space, USP <467> |
| (as Ethyl Acetate) | NMT 30 | | |
| (as Acetone) | | | |
| Lipid Composition | | | |
| Total Lipid (%) | 92.0-95.0 | QA - 86 | AOAC official method 933.08 |
| Chlorophyll (%) | NMT 1.50 | QA - 078 | Jeffrey & Humphrey (1975) - Photosynthetic pigments of Algae (1989) |
| Total carotenoids (%) | NMT 1.50 | QA - 85 | By JHFA method-1986 |
| Total Unsaponifiables (%) | NMT 12.0 | QA - 086 | AOAC official method 933.08 |
| Omega 3 [EPA + DHA] - % w/w | NLT 15.00 | QA - 087 | In House method |
| Total Omega 3 (% w/w) | NLT 17.00 | | |
| Total Omega 6 (% w/w) | NMT 5.00 | | |
| Total EFA (% w/w) | NLT 20. | | |
| Lipid percentage | | | |
| Triglycerides | 15-20% | | |
| Phospholipids | 5-10% | | |
| Glycolipids | 35-40% | | |
| Free fatty acids | 15-20% | | |
| Microbial parameters | | | |
| Standard Plate Count (cfu/1 g) | NMT 1,000 | QA - 039 | AOAC, 1995, Chapter 17 |
| Yeast & Mold (cfu/1 g) | NMT 100 | | |
| Coli forms (/10 g) | Negative | | |
| E. Coli (/10 g) | Negative | | |
| Staphylococcus (/10 g) | Negative | | |
| Salmonella (/10 g) | Negative | | |
| Fatty acid profile (Area %) | | | |
| Myristic acid [14.0] | NLT 4.0 | QA - 086 & 087 | In House GC method |
| Palmiltic acid [16:0] | NLT 16.0 | | |
| Palmito oleic acid [16:1, n-9] | NLT 12.0 | | |
| Hexadecadienoic acid [16:2, n-4] | NLT 4.0 | | |
| Hexadecatrienoic acid [16:3, n-4] | NLT 12.0 | | |
| Stearic acid [18:0] | NLT 0.10 | | |
| Oleic acid [18:1] | NLT 1.0 | | |
| Linoleic acid [18:2, n-6] - LA | NLT 1.0 | | |

| SPECIFICATION: ALGAE BASED OIL | | | |
|---|---|---|---|
| PARAMETERS | SPECIFICATION | SOP. NO | TEST METHOD/REFERENCE |
| AlphaLinolenic acid [18:3, n-3] - ALA | NLT 0.50 | | |
| Stearidonic acid [18:4, n-3] - SA | NLT 0.10 | | |
| Arachidonic Acid [20:4, n-6] - AA | NLT 0.25 | | |
| Eicosapentaenoic acid [20:5, n-3] | NLT 15.0 | | |
| Decosahexaenoic acid [20:6, n-3] | NLT 1.5 | | |
| Heavy Metals | | | |
| Lead (ppm) | NMT 1.0 | External | AOAC 18th |
| Arsenic (ppm) | NMT 0.5 | lab | Edn: 2006 By |
| Cadmium (ppm) | NMT 0.05 | reports | ICPMS |
| Mercury (ppm) | NMT 0.05 | | |

Safety: Safe for the intended use
Shelf life: 24 months from the date of manufacture
Stability: Stable in unopen conditions
Storage: Store in a cool, dry place away from sunlight, flush container with Nitrogen after use
Documentation: Every Batch of shipment carries COA
Packing: 1 kg, 5 kg, and 20 kg food grade containers

| FATTY ACID PROFILE CHART ALGAE BASED OIL | |
|---|---|
| FATTY ACID | ALGAE BASED OMEGA-3 (EPA) OIL |
| Total fatty acid, gm/100 gm of oil | 75 gm |
| Fatty acid [% of total fatty acid] | |
| Myristic acid [14:0] | 6.87 |
| Pentadecanoic acid [15:0] | NA |
| Palmitic acid [16:0] | 20.12 |
| Palmito oleic acid [16:1, ω-9] | 18.75 |
| Hexadeca dienoic acid [16:2, ω-4] | 6.84 |
| Hexadeca trienoic acid [16:4, ω-4] | 12.54 |
| Heptadecanoic acid [17:0] | NA |
| Stearic acid [18:0] | 0.68 |
| Oleic acid [18:1, ω-9] | 3.56 |
| Linoleic acid [18:2, ω-6] | 2.68 |
| Alpha linolenic acid [18:3, ω-3] | 3.73 |
| Gamma linolenic acid [18:3, ω-6] | NA |
| Stearidoni acid [18:4, ω-3] | 0.33 |
| Arachidonic acid [20:4, ω-6] | 0.97 |
| Eicosapentaenoic acid [20:5, ω-3] EPA | 23.00 |
| Docosapentaenoic acid [22:5, ω-3] DHA | NA |
| Docosahexaenoic acid [22:6, ω-3] DHA | 3.26 |
| others | 3.54 |
| EPA/DHA [gm/100 gm oil] | 15.75 |
| Total ω-3 fatty acids [gm/100 gm oil] | 18.20 |
| LIPD CLASS DETAILS [gm/100 gm oil] | |
| Unsaponifiables [carotenoids, chlorophyll, sterol, fatty alcohol etc.,] | 12 |
| Free fatty acids | 20 |
| Triglydcerides | 20 |
| Phospholipids | 10 |
| Glycolipids | 38 |
| Total | 100 |
| STABILITY [months] | 24 |

| FATTY ACID PROFILE - COMPARATIVE CHART NON-ALGAE BASED OILS | | | |
|---|---|---|---|
| FATTY ACID | FISH OIL MAXEPA | KRILL OIL | MARTEK OIL |
| Total fatty acid, gm/100 gm of oil | 95 gm | 70-80 gm | 95 gm |
| Fatty acid [% of total fatty acid] | | | |
| Myristic acid [14:0] | 8.68 | 11.09 | 11.47 |
| Pentadecanoic acid [15:0] | NA | NA | NA |
| Palmitic acid [16:0] | 20.35 | 22.95 | 26.36 |
| Palmito oleic acid [16:1, ω-9] | 11.25 | 6.63 | NA |
| Hexadeca dienoic acid [16:2, ω-4] | NA | NA | NA |
| Hexadeca trienoic acid [16:4, ω-4] | NA | NA | NA |
| Heptadecarioic acid [17:0] | NA | NA | NA |
| Stearic acid [18:0] | 4.67 | 1.02 | 0.50 |
| Oleic acid [18:1, ω-9] | 13.07 | 17.93 | 1.50 |
| Linoleic acid [18:2, ω-6] | 1.28 | 0.14 | 0.61 |
| Alpha linolenic acid [18:3, ω-3] | 0.33 | 2.11 | 0.40 |
| Gamma linolenic acid [18:3, ω-6] | NA | NA | NA |
| Stearidoni acid [18:4, ω-3] | 1.69 | 7.01 | 0.33 |
| Arachidonic acid [20:4, ω-6] | 0.50 | NA | NA |
| Eicosa pentaenoic acid [20:5, ω-3] EPA | 20.31 | 19.04 | 1.0 |
| Docosa pentaenoic acid [22:5, ω-3] DHA | NA | NA | 15.21 |
| Docosa hexaenoic acid [22:6, ω-3] DHA | 13.34 | 11.94 | 42.65 |
| others | 4.53 | 0.14 | NA |
| EPA/DHA [gm/100 gm oil] | 31.96 | 21.68 | 41.46 |
| Total ω-3 fatty acids [gm/100 gm oil] | 33.85 | 28.00 | 41.60 |
| LIPD CLASS DETAILS [gm/100 gm oil] | | | |
| Unsaponifiables [carotenoids, chlorophyll, sterol, fatty alcohol etc.,] | 5 | 5 | 5 |
| Free fatty acids | 0.5 | 30 | 0.5 |
| Triglydcerides | 94.5 | 25 | 94.5 |
| Phospholipids | Nil | 40 | Nil |
| Glycolipids | Nil | Nil | Nil |
| Total | 100 | 100 | 100 |
| STABILITY [months] | 12 | 24 | 6 |

Different types of marine based algae oils may be used, including *nannochloropsis oculata* as a source of EPA. Another algae that may be used is *thalassiosira weissflogii* such as described in U.S. Pat. No. 8,030,037 assigned to the above-mentioned Parry Nutraceuticals, a Division of EID Parry (India) Ltd., the disclosure which is hereby incorporated by reference in its entirety. Other types of algae as disclosed include *chaetoceros* sp. or *prymnesiophyta* or green algae such as *chlorophyta* and other microalgae that are *diamons tiatoms*. The *chlorophyta* could be *tetraselmis* sp. and include *prymnesiophyta* such as the class prymnesiophyceae and such as the order isochrysales and more specifically, *isochrysis* sp. or *pavlova* sp.

There are many other algae species that can be used to produce EPA and DHA as an algae based oil whether marine based or not to be used in accordance with a non-limiting example. In some cases, the isolation of the phospholipid and glycolipid bound EPA and DHA based oils may require manipulation of the algae species growth cycle.

Other algae/fungi phospholipid/glycolipid sources include: *grateloupia turuturu; porphyridium cruentum; monodus subterraneus; phaeodactylum tricornutum; isochrysis galbana; navicula* sp.; *pythium irregule; nannochloropsis* sp.; and *nitzschia* sp.

Details regarding *grateloupia turuturu* are disclosed in the article entitled, "*Grateloupia Turuturu* (Halymeniaceae, *Rhodophyta*) is the Correct Name of the Non-Native Species in the Atlantic Known as *Grateloupia Doryphora*," Eur. J. Phycol. (2002), 37: 349-359, as authored by Brigitte Gavio and Suzanne Fredericq, the disclosure which is incorporated by reference in its entirety.

*Porphyridium cruentum* is a red algae in the family porphyridiophyceae and also termed *rhodophyta* and is used as a source for fatty acids, lipids, cell-wall polysaccharides and pigments. The polysaccharides of this species are sulphated. Some *porphyridium cruentum* biomass contains carbohydrates of up to 57%.

*Monodus subterraneus* is described in an article entitled, "Biosynthesis of Eicosapentaenoic Acid (EPA) in the Fresh Water Eustigmatophyte *Monodus Subterraneus* (Eustigmatophyceae)," J. Phycol, 38, 745-756 (2002), authored by Goldberg, Shayakhmetova, and Cohen, the disclosure which is incorporated by reference in its entirety. The biosynthesis of PUFAs from algae is complicated and the biosynthesis from this algae is described in that article.

*Phaeodactylum tricornutum* is a diatom and unlike most diatoms, it can grow in the absence of silicon and the biogenesis of silicified frustules is facultative.

*Isochrysis galbana* is a microalgae and used in the bivalve aquaculture industry.

*Navicula* sp. is a boat-shaped algae and is a diatom. *Pythium irregule* is a soilborne pathogen found on plant hosts.

*Nannochloropsis* sp. occurs in a marine environment, but also occurs in fresh and brackish water. The species are small, nonmotile spheres that do not express any distinct morphological feature. These algae have chlorophyll A and lack chlorophyll B and C. They can build high concentrations of pigment such as astaxanthin, zeaxanthin and canthaxinthin. They are about 2-3 micrometers in diameter. They may accumulate high levels of polyunsaturated fatty acids.

*Nitzschia* sp. is a pinnate marine diatom and usually found in colder waters and associated with both Arctic and Antarctic polar sea ice where it is a dominant diatom. It produces a neurotoxin known as domoic acid which is responsible for amnesic shell fish poisoning. It may grow exponentially at temperatures between −4 and −6 degrees C. It may be processed to form and extrapolate the fatty acids.

As a source of polyunsaturated fatty acids, microalgae competes with other micro-organisms such as fungi and bacteria. There may be some bacterial strains that could be an EPA source, but microalgae has been found to be a more adequate and readily available source. Microalgae is a good source of oil and EPA when derived from *phaeodactylum, isochrysis* and *monodus*. The microalgae *phaeodactylum tricornutum* produces a high proportion of EPA. Other different strains and species of microalgae, fungi and possibly bacteria that can be used to source EPA include the following:

I. Diatoms
  *Asterionella japonica*
  *Bidulphia sinensis*
  *Chaetoceros septentrionale*
  *Lauderia borealis*
  *Navicula biskanteri*
  *Navicula laevis* (*heterotrof.*)
  *Navicula laevis*
  *Navicula incerta*
  *Stauroneis amphioxys*
  *Navicula pellicuolsa*
  *Biduiphia aurtia*
  *Nitzschia alba*
  *Nitzschia chosterium*
  *Phaeodactylum tricornutum*
  *Phaeodactylum tricornutum*
  *Skeletonema costatum*
II. Chrysophyceae
  *Pseudopedinella* sp.
  *Cricosphaera elongate*
III. Eustigmatophyceae
  *Monodus subterraneus*
  *Nannochloropsis*
IV. Prymnesiophyceae
  *Rodela violacea* 115.79
  *Porphyry. Cruentum* 1380.Id
V. Prasinophyceae
  *Pavlova salina*
VI. Dinophyceae
  *Cochlodinium heteroloblatum*
  *Cryptecodinium cohnii*
  *Gonyaulax catenella*
  *Gyrodinium cohnii*
  *Prorocentrum minimum*
VII. Other Microalgae
  *Chlorella minutissima*
  *Isochrysis galbana* ALII4
  *Phaeodactylum tricornutum* WT
  *Porphyridium cruentum*
  *Monodus subterraneus*
VIII. Fungi
  *Mortierella alpine*
  *Mortierella alpine* IS-4
  *Pythium irregulare*
IX. Bacteria
  SCRC-2738

Different microalgae may be used to form the algae based oil comprising glycolipids and phospholipids and at least EPA and/or EPA/DHA. Examples include: *Chlorophyta, Cyanophyta* (Cyanobacteria), and *Heterokontophyta*. The microalgae may be from one of the following classes: Bacillariophyceae, Eustigmatophyceae, and Chrysophyceae. The microalgae may be from one of the following genera: *Nannochioropsis, Chlorella, Dunaliella, Scenedesmus, Selenastrum, Oscillatoria, Phormidium, Spirulina, Amphora*, and *Ochromonas*.

Other non-limiting examples of microalgae species that may be used include: *Achnanthes orientalis, Agmenellum* spp., *Amphiprora hyaline, Amphora coffeiformis, Amphora coffeiformis* var. *linea, Amphora coffeiformis* var. *punctata, Amphora coffeiformis* var. *taylori, Amphora coffeiformis* var. *tenuis, Amphora delicatissima, Amphora delicatissima* var. *capitata, Amphora* sp., *Anabaena, Ankistrodesmus, Ankistrodesmus falcatus, Boekelovia hooglandii, Borodinella* sp., *Botryococcus braunii, Botryococcus sudeticus, Bracteococcus minor, Bracteococcus medionucleatus, Carteria, Chaetoceros gracilis, Chaetoceros muelleri, Chaetoceros muelleri* var. *subsalsum, Chaetoceros* sp., *Chlamydomas perigranulata, Chlorella anitrata, Chlorella antarctica, Chlorella aureoviridis, Chlorella candida, Chlorella capsulate, Chlorella desiccate, Chlorella ellipsaidea, Chlorella emersonii, Chlorella fusca, Chlorella fusca* var. *vacuolata, Chlorella glucotropha, Chlorella infusionum, Chlorella infusionum* var. *actophila, Chlorella infusionum* var. *auxenophila, Chlorella kessleri, Chlorella lobophora, Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides, Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella saline, Chlorella simplex, Chlorella sorokiniana, Chlorella* sp., *Chlorella sphaerica, Chlorella stigmatophora, Chlorella vanniellii, Chlorella vulgaris, Chlorella vulgaris* fo. *tertia, Chlorella vulgaris* var. *autotrophica, Chlorella vulgaris* var. *viridis, Chlorella vulgaris* var. *vulgaris, Chlorella vulgaris* var. *vulgaris* fo. *tertia, Chlorella vulgaris* var. *vulgaris* fo. *viridis, Chlorella xanthella, Chlorella zofingiensis, Chlorella trebouxioides, Chlorella vulgaris, Chlorococcum infusionum, Chlorococcum* sp., *Chlorogonium, Chroomonas* sp., *Chrysosphaera* sp., *Cricosphaera* sp., *Crypthecodinium cohnii, Cryptomonas* sp., *Cyclotella cryptica, Cyclotella meneghiniana, Cyclotella* sp., *Dunaliella* sp., *Dunaliella bardawil, Dunaliella bioculata, Dunaliella granulate, Dunaliella maritime, Dunaliella minute, Dunaliella parva, Dunaliella peircei, Dunaliella primolecta, Dunaliella saline, Dunaliella terricola, Dunaliella tertiolecta, Dunaliella viridis, Dunaliella tertiolecta, Eremosphaera viridis, Eremosphaera* sp., *Effipsoidon* sp., *Euglena* spp., *Franceia* sp., *Fragilaria crotonensis, Fragilaria* sp., *Gleocapsa* sp., *Gloeothamnion* sp., *Haematococcus pluvialis, Hymenomonas* sp., *Isochrysis aff. galbana, Isochrysis galbana, Lepocinclis, Micractinium, Micractinium, Monoraphidium minutum, Monoraphidium* sp., *Nannochloris* sp., *Nannochlopsis saline, Nannochloropsis* sp., *Navicula acceptata, Navicula biskanterae, Navicula pseudotenelloides, Navicula pelliculosa, Navicula saprophila, Navicula* sp., *Nephrochloris* sp., *Nephroselmis* sp., *Nitschia communis, Nitzschia alexandrina, Nitzschia closterium, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscillatoria limnetica, Oscillatoria* sp., *Oscillatoria subbrevis, Parachlorella kessleri, Pascheria acidophila, Pavlova* sp., *Phaeodactylum tricomutum, Phagus, Phormidium, Platymonas* sp., *Pleurochrysis carterae, Pleurochrysis dentate, Pleurochrysis* sp., *Prototheca wickerhamii, Prototheca stagnora, Prototheca portoricensis, Prototheca moriformis, Prototheca zopfii, Pseudochiorella aquatica, Pyramimonas* sp., *Pyrobotrys, Rhodococcus opacus, Sarcinoid chrysophyte, Scenedesmus armatus, Schizochytrium, Spirogyra, Spirulina platensis, Stichococcus* sp., *Synechococcus* sp., *Synechocystisf, Tagetes erecta, Tagetes patula, Tetraedron, Tetraselmis* sp., *Tetraselmis suecica, Thalassiosira weissflogii*, and *Viridiella fridericiana*. Preferably, the microalgae are autotrophic.

It is also possible to form the oil comprising glycolipids and phospholipids and at least EPA from genetically modified yeast. Non-limiting examples of yeast that can be used include: *Cryptococcus curvatus, Cryptococcus terricolus, Lipomyces starkeyi, Lipomyces lipofer, Endomycopsis vernalis, Rhodotorula glutinis, Rhodotorula gracilis, Candida 107, Saccharomyces paradoxus, Saccharomyces mikatae, Saccharomyces bayanus, Saccharomyces cerevisiae*, any *Cryptococcus, C. neoformans, C. bogoriensis, Yarrowia lipolytica, Apiotrichum curvatum, T. bombicola, T. apicola, T. petrophilum, C. tropicalis, C. lipolytica*, and *Candida albicans*. It is even possible to use a biomass as a wild type or genetically modified fungus. Non-limiting examples of fungi that may be used include *Mortierella, Mortierrla vinacea, Mortierella alpine, pythium debaryanum, Mucor circinelloides, Aspergillus ochraceus, Aspergillus terreus, Pennicillium iilacinum, Hensenulo, Chaetomium, Cladosporium, Malbranchea, Rhizopus*, and *Pythium*.

It is also possible that bacteria may be used that includes lipids, proteins, and carbohydrates, whether naturally occurring or by genetic engineering. Non-limiting examples of bacteria include: *Escherichia coli, Acinetobacter* sp. any actinomycete, *Mycobacterium tuberculosis*, any streptomycete, *Acinetobacter calcoaceticus, P. aeruginosa, Pseudomonas* sp., *R. erythropolis, N. erthopolis, Mycobacterium* sp., B., *U. zeae, U. maydis, B. lichenformis, S. marcescens, P. fluorescens, B. subtilis, B. brevis, B. polmyma, C. lepus, N. erthropolis, T. thiooxidans, D. polymorphis, P. aeruginosa* and *Rhodococcus opacus*.

Possible algae sourced, EPA/DHA based oils that are derived from an algae and contain glycol and phospholipid bound EPA and/or EPA/DHA and may include a significant amount of free fatty acids, triglycerides and phospholipids and glycolipids in the range of 35-40% or more of total lipids are disclosed in the treatise "Chemicals from Microalgae" as edited by Zvi Cohen, CRC Press, 1999. Reference is also made to a study in men that have been given a single dose of oil from a polar-lipid rich oil from the algae *nannochloropis oculata* as a source of EPA and described in the article entitled, "Acute Appearance of Fatty Acids in Human Plasma—A Comparative Study Between Polar-Lipid Rich Oil from the Microalgae *Nannochloropis Oculata* in Krill Oil in Healthy Young Males," as published in Lipids in Health and Disease, 2013, 12:102 by Kagan et al. The EPA in that algae oil was higher than that of krill oil by about 25.06 to 13.63 for fatty acid composition as the percent of oil. The algae oil was provided at 1.5 grams of EPA and no DHA as compared to krill oil that was provided at 1.02 grams EPA and 0.54 grams DHA. The participants consumed both oils in random order and separated by seven days and the blood samples were collected before breakfast and at several time points up to 10 hours after taking the oils.

The researchers determined that the algae based oil had a greater concentration of EPA and plasma than krill oil with the EPA concentration higher with the algae based oil at 5, 6, 8 and 10 hours (P<0.05) intended to be higher at 4 hours (P=0.094). The maximum concentration (CMAX) of EPA was higher with algae oil than with krill oil (P=0.010). The maximum change in concentration of EPA from its fasting concentration was higher than with krill oil (P=0.006). The area under the concentration curve (AUC) and the incremental AUC (IAUC) was greater (P=0.020 and P=0.006). This difference may relate to the different chemical composition and possibly the presence of the glycolipids where the presence of DHA in krill oil limits the incorporation of EPA into plasma lipids. Also, the n-3 polyunsaturated fatty acids within glycolipids as found in the algae oil, but not in a krill oil, may be an effective system for delivering EPA to humans.

The incorporated by reference '037 patent describes the benefit of using an algae based oil, and more particularly, a marine based algae oil and discloses different manufacturing and production techniques. Microalgae can be cultured photoautotrophically outdoors to prepare concentrated microalgae products containing Eicosapentaenoic acid (EPA) and Docosahexaenoic acid (DHA), which are the long-chain polyunsaturated fatty acids (PUFAs) found in fish oil. Both are very important for human and animal health. The concentrated microalgae products as disclosed in the '037 patent may contain EPA and DHA and lipid products containing EPA and DHA purified from microalgae. The concentrated microalgae composition may be prepared by cultivating microalgae photoautotrophically outdoors in open ponds under filtered sunlight in a continuous or batch mode and at a dilution rate of less than 35% per day. The microalgae may be harvested in the exponential phase when the cell number is increasing at a rate of at least 20% of maximal rate. In one example, the microalgae is concentrated. In another example, at least 40% by weight of lipids in the microalgae are in the form of glycodiacyiglycerides, phosphodiacyiglycerides, or a combination thereof and at least 5% by weight of the fatty acids are DHA, EPA, or a combination thereof.

In one example, the microalgae are *Tetraselmis* sp. cultivated at above 20° C. or in another example at above 30° C. The EPA yield in the microalgae has been found to be at least 10 mg/liter culture. The microalgae can be *Isochrysis* sp. or *Pavlova* sp. in another example, or are *Thalassiosira* sp. or *Chaetecoros* sp. The microalgae may be different diatoms and are cultivated photoautotrophically outdoors in open ponds for at least 14 days under filtered sunlight and at least 20% by weight of the fatty acids are EPA.

The use of this algae based oil overcomes the technical problems associated with the dwindling supplies of fish oil and/or Antarctic krill, which are now more difficult to harvest and obtain and use economically because these products are in high demand. A major difference between fish oils and algae based oils is their structure. Fish oils are storage lipids and are in the form of triacylglycerides. The algae based oils as lipids are a mixture of storage lipids and membrane lipids. The EPA and DHA present in algae based oils is mainly in the form of glycolipids and a small percentage is in the form of phospholipids. Glycolipids are primarily part of chloroplast membranes and phospholipids are part of cell membranes.

The incorporated by reference '037 patent describes various methods for culturing microalgae photoautotrophically outdoors to produce EPA and DHA. One method used is filtering sunlight to reduce the light intensity on the photoautotrophic culture. Shade cloth or netting can be used for this purpose. It was determined that for most strains, the optimal solar intensity for growth, for maintaining a pure culture, and for omega-3 fatty acid accumulation was about 40,000 to 50,000 lux, approximately half of the 110,000 lux of full sunlight. Shade cloth or netting is suitable for filtering the sunlight to the desired intensity.

It is also possible to culture microalgae photoautotrophically outdoors and produce EPA and DHA by using small dilutions and a slow dilution rate of less than 40% per day, preferably less than 35% per day, more preferably from about 15% to about 30% per day. In other examples, the dilution rate is 15-40% per day or 15-35% per day, and in yet other examples, the dilution rate is 10-30%, 10-35%, or 10-40% per day. These smaller dilutions and lower dilution rates than are usually used help prevent contamination in outdoor photoautotrophic cultures. It also promotes thick culture growth that gives good DHA or EPA yield.

Another technique to successfully culture microalgae photoautotrophically outdoors and produce EPA and EPA/DHA is to harvest the microalgae in exponential phase rather than stationary phase. Harvesting in exponential phase reduces the risk of contamination in outdoor photoautotrophic cultures and has surprisingly been found to give a good yield of EPA and DHA. To drive fat accumulation in microbial cultures, the cultures are harvested in stationary phase because cells in the stationary phase tend to accumulate storage lipids. The '037 patent teaches that EPA and DHA accumulate in large amounts as membrane lipids in cultures harvested in the exponential phase. The membrane lipids containing EPA and DHA are predominantly phosphodiacylglycerides and glycodiacyiglycerides, rather than the triaclyglycerides found in storage lipids. These cultures are harvested often when cell number is increasing at a rate at least 20% of the maximal rate, i.e., the maximal rate achieved at any stage during the outdoor photoautotrophic growth of the harvested culture. In specific examples, the cultures are harvested in exponential phase when cell number is increasing at a rate of at least 30%, at least 40%, or at least 50% of maximal rate. It is also possible to use recombinant DNA techniques.

The incorporated by reference '037 patent includes several examples, which are referenced to the reader for description and teaching purposes as Examples 1-6.

It is possible to also add and use a shrimp oil that is extracted from shrimp mince and shells that include high levels of phospholipids and omega-3 fatty acids such as EPA and DHA. The oils may be rich in astaxanthin. The parts per million of astaxanthin can range from 3,000 to 7,000, and in one example, from 3,500 to 6,000 parts per million. Total phospholipids may be about 25-35% w/w. The total omega-3 may be greater than about 16.0 grams per 1,000 grams with an EPA percentage of greater than 17% and about greater than 8 grams per 100 grams of the DHA percent of greater than 14. These ranges can vary, of course.

The oils may be supplemented with astaxanthin. Four milligrams of astaxanthin per day for two weeks could be supplemented. 0.1 to 50 mg of astaxanthin may be supplemented to an oil per daily dose including about 0.1 to 12 mg of astaxanthin and another example of 0.5 to 8 mg. The astaxanthin may be derived from *Haematococcus pluvialis* algae, *pfaffia*, krill or other synthetic routes in a known free diol, monoester or diester form.

It is also possible to use a pure diol of the S, S'astaxanthin. It is possible to use that pure diol in combination with the EPA rich algae based oil as described above and which is admixed with either astaxanthin derived from *Haematococcus pluvialis* or the free diol form in substantially pure S,S' enantiomer form. It is possible to add synthetically derived mixed enantiomers of the diol as a product that is sold as a fish food in one non-limiting example. The diol of the S, S'astaxanthin is possible because in both cases of krill oil and possibly the algae based oil and Hp derived, there are principally diesters and monoesters respectively with very little diol, which is insoluble. Some research indicates that it may be many times more bioavailable than either the monoester or diester form. It is possible to asymmetrically synthesize the S,S' pure diol. Despite the pure diol's poor solubility in some examples, there may be an active transport mechanism related to its bioavailability, or conversely, that only in the diol form is the monoester or diester forms transferred from the intestines to the blood. The phospholipid or glycolipid based product presenting EPA and/or DHA along with the added astaxanthin in its various forms and especially the S,S' enantiomeric form in principally monoester form from *Haematococcus pluvialis* or pure diol form from asymmetric synthesis could be viable. Thus, it is possible to combine it with the algae derived glycol and phospholipid based EPA rich oil.

Possible uses of the composition include use as a treatment for depression that may counter neurological disorders associated with depression. This could include treatment for a deficiency of neurotransmitters at post-synaptic receptor sites. The composition may be used to treat manic episodes in bipolar treatments and treat panic disorder and reduce the frequency and severity of panic attacks and the severity of agoraphobia. The composition may be used to treat Obsessive Compulsive Disorder (OCD) and malfunctioning neurotransmitters and serotonin receptors. The composition may also be used in the treatment of Alzheimer's Disease (AD) and reduce the presence of aluminosilicates at the core of senile plaque and diseased neurons. The composition may be used to treat aging disorders for cellular differentiation, proliferation and regeneration. It may also be used to treat age-related changes in mitochondrial function and age-related hearing loss. The composition may also possibly maintain metabolic activity and available energy by maintaining levels of phospholipids in normal cells and maintain membrane integrity and regulate enzyme activities and membrane transport processes through changes in membrane fluidity.

The composition may be beneficial for biological functions of essential fatty acids, including neural tissues such as the brain and retina and treat dementia-related diseases to increase mental function, memory, concentration and judgment and overcome the effects of Alzheimer's Disease. The composition may also be used to restore and preserve liver function and protect the liver against damage from alcoholism, pharmaceuticals, pollutant substances, viruses and other toxic influences that may damage cell membranes. It may possibly have antioxidant activity.

Additives may be used with the reaction composition and pharmaceutical or nutraceutical formulations may be made by methods known in the art. For example, the composition may be formulated in a conventional manner using one or more pharmaceutically or nutraceutically acceptable carriers. Thus, the composition may be formulated for oral administration. For oral administration, the pharmaceutical or nutraceutical compositions as compositions may take the form of, for example, tablets or capsules prepared by conventional techniques with pharmaceutically or nutraceutically acceptable excipients such as binding agents (e.g., pregelatinised maize starch, polyvinylpyrrolidone or hydroxypropyl methylcellulose); filters (e.g., lactose, microcrystalline cellulose or calcium phosphate); lubricants (e.g., magnesium stearate, talc or silica); disintegrants (e.g., potato starch or sodium starch glycollate); or wetting agents (e.g., sodium lauryl sulphate). The tablets may be coated by methods known in the art. Liquid preparations for oral administration may take the form of, for example, solutions, syrups or suspensions, or they may be presented as a dry product for use with water or another suitable vehicle before use. Such liquid preparations may be prepared by conventional techniques with pharmaceutically or nutraceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

When the composition is used as a nutraceutical, it can be in the form of foods, beverages, energy bars, sports drinks, supplements or other forms as known in the art. This composition is also useful in cosmetic preparations, e.g., moisturizing creams, sun-block products and other topical cosmetic products as known in the art.

The composition may possibly be used in the treatment or prevention of a variety of disease states including: liver disease; chronic hepatitis; steatosis; liver fibrosis; alcoholism; malnutrition; chronic parenteral nutrition; phospholipid deficiency; lipid peroxidation; disarrhythmia of cell regeneration; destabilization of cell membranes; coronary artery disease caused by hypercholesterolemia; high blood pressure; menopausal or post-menopausal conditions; cancer, e.g., skin cancer; hypertension; aging; benign prostatic hyperplasia; kidney disease; edema; skin diseases; gastrointestinal diseases; peripheral vascular system diseases (e.g. leg ulcers); pregnancy toxemia; and neurodegenerative and psychiatric diseases (e.g. Parkinson's, Alzheimer's, autism, attention deficit disorder, learning disorders, mood disorders, bipolar depression, multiple sclerosis, muscular dystrophy).

The composition may also be useful for targeting tumors and may be used in conjunction with radioisotopes for diagnosing central nervous system tumors. The composition may also be used to reduce local fat deposits and reducing visible cellulite. The composition may also be used in aesthetics such as breast enlargement by acting on the lobular tissue of the breast and by increasing hydration of the breast.

The composition may be used to treat and/or prevent cardiovascular diseases, arthritis, skin cancer, diabetes, premenstrual syndrome and transdermal transport enhancement. It may be used to decrease cholesterol in vivo and inhibit platelet adhesion and plaque formation and reduce vascular endothelial inflammation in a patient and offer hypertension prophylaxis. The composition may prevent oxidation of low-density lipoprotein and have an inhibitory effect on the secretion of VLDL possibly due to increased intracellular degradation of APO B-100. It may offer a post-myocardial infarction prophylaxis possibly because of its ability to decrease CIII apolipoprotein B, to decrease C3 non-apoliproprotein B lipoproteins and to increase antithrombin 3 levels. It may be suitable for prophylactic usage against cardiovascular disease in humans where it relates to coronary disease, hyperlipidemia, hypertension, ischemic disease such as relating to angina, myocardial infarction, cerebral ischemia, and shock without clinical or laboratory evidence of ischemia or arrhythmia.

The composition may be suitable to offer symptomatic relief for arthritis, Still's Disease, polyarticular or pauciarticular juvenile rheumatoid arthritis, rheumatoid arthritis, osteoarthritis, and may provide clinical improvement in decreasing the number of tender joints and analgesics consumed daily by decreasing the production of interleukin and interleukin-1 in human patients. The composition may also be used as a skin cancer prophylactic. It may have some retinal and anti-carcinogenic effects. It may enhance transdermal transportation as a substrate for dermatological topical therapeutic applications and may be used in dermatological treatments via creams, ointments, gels, lotions and oils and may be used in various therapeutic applications such as relating to anesthesic, corticosteroids, anti-inflammatory, antibiotic and ketolytic functions. It may also be used to enhance transdermal transportation as a substrate for dermatological topical cosmetic applications where cosmetic application relates to skin hydration, anti-wrinkle, caratolytics, peeling and mask via creams, ointments, gels, lotions or oils. The composition may be used to reduce the pain and mood changes associated with premenstrual syndrome in women.

The composition may be used to treat or prevent a cardiometabolic disorder/metabolic syndrome. The cardiometabolic disorder could be atherosclerosis, arteriosclerosis, coronary heart (carotid artery) disease (CHD or CAD), acute coronary syndrome (or ACS), valvular heart disease, aortic and mitral valve disorders, arrhythmia/atrial fibrillation, cardiomyopathy and heart failure, angina pectoris, acute myocardial infarction (or AMI), hypertension, orthostatic hypotension, shock, embolism (pulmonary and venous), endocarditis, diseases of arteries, the aorta and its branches, disorders of the peripheral vascular system (peripheral arterial disease or PAD), Kawasaki disease, congenital heart disease (cardiovascular defects) and stroke (cerebrovascular disease), dyslipidemia, hypertriglyceridemia, hypertension, heart failure, cardiac arrhythmias, low HDL levels, high LDL levels, stable angina, coronary heart disease, acute myocardial infarction, secondary prevention of myocardial infarction, cardiomyopathy, endocarditis, type 2 diabetes, insulin resistance, impaired glucose tolerance, hypercholesterolemia, stroke, hyperlipidemia, hyperlipoproteinemia, chronic kidney disease, intermittent claudication, hyperphosphatemia, omega-3 deficiency, phospholipid deficiency, carotid atherosclerosis, peripheral arterial disease, diabetic nephropathy, hypercholesterolemia in HIV infection, acute coronary syndrome (ACS), non-alcoholic fatty liver disease/non-alcoholic steatohepatitis (NAFLD/NASH), arterial occlusive diseases, cerebral atherosclerosis, arteriosclerosis, cerebrovascular disorders, myocardial ischemia, coagulopathies leading to thrombus formation in a vessel and diabetic autonomic neuropathy.

The composition may also be used to treat, prevent or improve cognition and/or a cognitive disease, disorder or impairment (memory, concentration, learning (deficit)), or of treating or preventing neurodegenerative disorders. The cognitive disease, disorder or impairment could be Attention Deficit Disorder (ADD), Attention Deficit Hyperactivity Disorder (ADHD), autism/autism spectrum disorder (ASD), (dyslexia, age-associated memory impairment and learning disorders, amnesia, mild cognitive impairment, cognitively impaired non-demented, pre-Alzheimer's disease, Alzheimer's disease, epilepsy, Pick's disease, Huntington's disease, Parkinson disease, Lou Gehrig's disease, pre-dementia syndrome, Lewy body dementia dementia, dentatorubropallidoluysian atrophy, Freidreich's ataxia, multiple system atrophy, types 1, 2, 3, 6, 7 spinocerebellar ataxia, amyotrophic lateral sclerosis, familial spastic paraparesis, spinal muscular atrophy, spinal and bulbar muscular atrophy, age-related cognitive decline, cognitive deterioration, moderate mental impairment, mental deterioration as a result of ageing, conditions that influence the intensity of brain waves and/or brain glucose utilization, stress, anxiety, concentration and attention impairment, mood deterioration, general cognitive and mental well being, neurodevelopmental, neurodegenerative disorders, hormonal disorders, neurological imbalance or any combinations thereof. The cognitive disorder may be memory impairment.

The composition may be used to inhibit, prevent or treat inflammation or an inflammatory disease. The inflammation or inflammatory disease may be due to organ transplant rejection; reoxygenation injury resulting from organ transplantation (see Grupp et al., J. Mol. Cell. Cardiol. 31: 297-303 (1999)) including, but not limited to, transplantation of the following organs: heart, lung, liver and kidney; chronic inflammatory diseases of the joints, including arthritis, rheumatoid arthritis, osteoarthritis and bone diseases associated with increased bone resorption; inflammatory bowel diseases (IBD) such as ileitis, ulcerative colitis (UC), Barrett's syndrome, and Crohn's disease (CD); inflammatory lung diseases such as asthma, acute respiratory distress syndrome (ARDS), and chronic obstructive pulmonary disease (COPD); inflammatory diseases of the eye including corneal dystrophy, trachoma, onchocerciasis, uveitis, sympathetic ophthalmitis and endophthalmitis; chronic inflammatory diseases of the gum, including gingivitis and periodontitis; inflammatory diseases of the kidney including uremic complications, glomerulonephritis and nephrosis; inflammatory diseases of the skin including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, epilepsy, amyotrophic lateral sclerosis and viral or autoimmune encephalitis, preeclampsia; chronic liver failure, brain and spinal cord trauma, and cancer. The inflammatory disease may also be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is administered as a treatment for cancer. Other disorders include depression, obesity, allergic diseases, acute cardiovascular events, muscle wasting diseases, and cancer cachexia. Also, inflammation that results from surgery and trauma may possibly be treated.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that the modifications and embodiments are intended to be included within the scope of the dependent claims.

That which is claimed is:

1. A dietary supplement composition, comprising a therapeutically effective amount of a shelf stable, *perilla* seed oil extract derived from supercritical CO2 fluid extraction of a cracked biomass of *perilla* frutescens seed, astaxanthin, and lutein and trans-zeaxanthin, wherein the dietary supplement composition is formulated into a single dosage capsule, and wherein the astaxanthin is about 0.1 to 16 percent by weight of the *perilla* seed oil extract, the lutein is about 0.4 to 30 percent by weight of the *perilla* seed oil extract, and the trans-zeaxanthin is about 0.04 to 24 percent by weight of the *perilla* seed oil extract.

2. The composition according to claim 1, wherein the composition comprises 0.5 to 8 mg of astaxanthin, 2 to 15 mg of lutein and 0.2 to 12 mg of trans-zeaxanthin.

3. The composition according to claim 2, wherein the composition comprises about 4 mg of astaxanthin, about 10 mg of lutein and about 1.2 mg of trans-zeaxanthin.

4. The composition according to claim 1, wherein the composition comprises about 50 to 500 mg of *perilla* seed oil extract.

5. The composition according to claim 1, wherein the astaxanthin comprises 3S, 3'S-astaxanthin derived from *Haematococcus pluvialis*.

6. The composition according to claim 1, further comprising krill oil.

7. The composition according to claim 1, further comprising an algae based oil.

8. The composition according to claim 1, wherein the *perilla* seed oil extract comprises from about 60 to 95 percent w/w of PUFAs in a ratio of from about 4:1 to about 6:1 alpha-linolenic acid (ALA) to linoleic acid (LA).

9. The composition according to claim 1, wherein the peroxide value of the *perilla* seed oil extract is under 10.0 meq/Km.

\* \* \* \* \*